United States Patent [19]

Skerra et al.

[11] Patent Number: 5,506,121
[45] Date of Patent: Apr. 9, 1996

[54] FUSION PEPTIDES WITH BINDING ACTIVITY FOR STREPTAVIDIN

[75] Inventors: Arne Skerra, Wiesbaden; Thomas Schmidt, Luxembourg, both of Germany

[73] Assignee: Institut Für Bioanalytik Gemeinnützige Gesellschaft MBH, Gottingen, Germany

[21] Appl. No.: 148,675

[22] Filed: Nov. 3, 1993

[30] Foreign Application Priority Data

Nov. 3, 1992 [DE] Germany .................. 42 37 113.9

[51] Int. Cl.$^6$ .............. C07K 19/00; E12N 15/62
[52] U.S. Cl. .......... 435/69.7; 435/252.3; 435/320.1; 530/350; 530/412; 536/23.4
[58] Field of Search ............... 435/69.7, 252.3, 435/320.1; 530/350, 412; 536/23.4

[56] References Cited

PUBLICATIONS

Science 249: 404–406, 27 Jul. 1990, Devlin et al Random Peptide Libraries: A Source of Specific Protein Bonding Molecules.
Meth. In. Enzym. 185:129–142, 1990, Uhleu et al Gene Fusions for Purpose of Expression: An Introduction.
Bio Techniques 12: 264–268, Feb. 1992, Cano et al. DNA Hybridization Assay Using AttoPhos®, A Fluorescent Substrate for Alkaline Phosphatase.
Schmidt, et al., "The random peptide library–assisted engineering of a C–terminal affinity peptide, useful for the detection and purification of a functional Ig Fv fragment", *Protein Engineering* vol. 6, No. 1, pp. 109=14 122 (1993).

Primary Examiner—Garnette D. Draper
Assistant Examiner—John D. Ulm
Attorney, Agent, or Firm—Felfe & Lynch

[57] ABSTRACT

A peptide according to the invention comprises the amino acid sequence

Trp—X—His—Pro—Gln—Phe—Y—Z, in which X represents any desired amino acid and Y and Z either both denote Gly, or Y denotes Glu and Z denotes Arg or Lys. A fusion protein according to the invention consists of the amino acid sequence of a complete protein, of a protein mutant such as a deletion mutant or substitution mutant, or of part of a protein linked to the sequence of a peptide of the invention. For the production of a recombinant protein by expression of a DNA sequence coding therefor in suitable host cells according to well-known methods, a DNA sequence is used which codes for a fusion protein and, if desired, the presence of the expression product is detected by means of a conjugate of streptavidin and a label or the desired protein is separated as a fusion protein by means of streptavidin affinity chromatography.

14 Claims, 28 Drawing Sheets

FIG. 1A

```
      GCGCCCAATACGCAAACCGCCTCTCCCCGCGCGTTGGCCGATTCATTAATGCAGCTGGCA
  1   ---------+---------+---------+---------+---------+---------+ 60
      CGCGGGTTATGCGTTTGGCGGAGAGGGGCGCGCAACCGGCTAAGTAATTACGTCGACCGT a:    AlaProAsnThrGlnThrAlaSerProArgAlaLeuAlaAspSerLeuMetGlnLeuAla    -
b:      ArgProIleArgLysProProLeuProAlaArgTrpProIleHisEndCysSerTrpHis  -
c:        AlaGlnTyrAlaAsnArgLeuSerProArgValGlyArgPheIleAsnAlaAlaGlyThr -

CGACAGGTTTCCCGACTGGAAAGCGGGCAGTGAGCGCAACGCAATTAATGTGAGTTAGCT
 61   ---------+---------+---------+---------+---------+---------+ 120
      GCTGTCCAAAGGGCTGACCTTTCGCCCGTCACTCGCGTTGCGTTAATTACACTCAATCGA a:    ArgGlnValSerArgLeuGluSerGlyGlnEndAlaGlnArgAsnEndCysGluLeuAla    -
b:      AspArgPheProAspTrpLysAlaGlySerGluArgAsnAlaIleAsnValSerEndLeu  -
c:        ThrGlyPheProThrGlyLysArgAlaValSerAlaThrGlnLeuMetEndValSerSer -

CACTCATTAGGCACCCCAGGCTTTACACTTTATGCTTCCGGCTCGTATGTTGTGTGGAAT
121   ---------+---------+---------+---------+---------+---------+ 180
      GTGAGTAATCCGTGGGGTCCGAAATGTGAAATACGAAGGCCGAGCATACAACACACCTTA a:    HisSerLeuGlyThrProGlyPheThrLeuTyrAlaSerGlySerTyrValValTrpAsn    -
b:      ThrHisEndAlaProGlnAlaLeuHisPheMetLeuProAlaArgMetLeuCysGlyIle  -
c:        LeuIleArgHisProArgLeuTyrThrLeuCysPheArgLeuValCysCysValGluLeu -

H
                                                  i
                                                  n
                                                  d
                                                  I
                                                  I
                                                  I
      TGTGAGCGGATAACAATTTCACACAGGAAACAGCTATGACCATGATTACGCCAAGCTTGC
181   ---------+---------+---------+---------+---------+---------+ 240
      ACACTCGCCTATTGTTAAAGTGTGTCCTTTGTCGATACTGGTACTAATGCGGTTCGAACG a:    CysGluArgIleThrIleSerHisArgLysGlnLeuEndProEndLeuArgGlnAlaCys    -
b:      ValSerGlyEndGlnPheHisThrGlyAsnSerTyrAspHisAspTyrAlaLysLeuAla  -
c:        EndAlaAspAsnAsnPheThrGlnGluThrAlaMetThrMetIleThrProSerLeuHis -

ATGCAAATTCTATTTCAAGGAGACAGTCATAATGAAATACCTATTGCCTACGGCAGCCGC
241   ---------+---------+---------+---------+---------+---------+ 300
      TACGTTTAAGATAAAGTTCCTCTGTCAGTATTACTTTATGGATAACGGATGCCGTCGGCG a:    MetGlnIleLeuPheGlnGlyAspSerHisAsnGluIleProIleAlaTyrGlySerArg    -
b:      CysLysPheTyrPheLysGluThrValIleMetLysTyrLeuLeuProThrAlaAlaAla  -
c:        AlaAsnSerIleSerArgArgGlnSerEndEndAsnThrTyrCysLeuArgGlnProLeu -
```

FIG. 1B

```
                                                            E
                                                            c
                                                            o
                                                            O P
                                                   p        l p
                                                   s        0 u
                                                   t        9 M
                                                   I         I I
                                                              /
     TGGATTGTTATTACTCGCTGCCCAACCAGCGATGGCCCAGGTGCAGCTGCAGGAGTCAGG
301  ---------+---------+---------+---------+---------+---------+ 360
     ACCTAACAATAATGAGCGACGGGTTGGTCGCTACCGGGTCCACGTCGACGTCCTCAGTCC a: TrpIleValIleThrArgCysProThrSerAspGlyProGlyAlaAlaAlaGlyValArg  -
  b:  GlyLeuLeuLeuLeuAlaAlaGlnProAlaMetAlaGlnValGlnLeuGlnGluSerGly -
  c:   AspCysTyrTyrSerLeuProAsnGlnArgTrpProArgCysSerCysArgSerGlnAsp -

N
                           a
                           r
                           I
     ACCTGGCCTGGTGGCGCCCTCACAGAGCCTGTCCATCACATGCACCGTCTCAGGGTTCTC
361  ---------+---------+---------+---------+---------+---------+ 420
     TGGACCGGACCACCGCGGGAGTGTCTCGGACAGGTAGTGTACGTGGCAGAGTCCCAAGAG a: ThrTrpProGlyGlyAlaLeuThrGluProValHisHisMetHisArgLeuArgValLeu  -
  b:  ProGlyLeuValAlaProSerGlnSerLeuSerIleThrCysThrValSerGlyPheSer -
  c:   LeuAlaTrpTrpArgProHisArgAlaCysProSerHisAlaProSerGlnGlySerHis -

ATTAACCGGCTATGGTGTAAACTGGGTTCGCCAGCCTCCAGGAAAGGGTCTGGAGTGGCT
421  ---------+---------+---------+---------+---------+---------+ 480
     TAATTGGCCGATACCACATTTGACCCAAGCGGTCGGAGGTCCTTTCCCAGACCTCACCGA a: IleAsnArgLeuTrpCysLysLeuGlySerProAlaSerArgLysGlySerGlyValAla  -
  b:  LeuThrGlyTyrGlyValAsnTrpValArgGlnProProGlyLysGlyLeuGluTrpLeu -
  c:   EndProAlaMetValEndThrGlyPheAlaSerLeuGlnGluArgValTrpSerGlyTrp -

GGGAATGATTTGGGGTGATGGAAACACAGACTATAATTCAGCTCTCAAATCCAGACTGAG
481  ---------+---------+---------+---------+---------+---------+ 540
     CCCTTACTAAACCCCACTACCTTTGTGTCTGATATTAAGTCGAGAGTTTAGGTCTGACTC a: GlyAsnAspLeuGlyEndTrpLysHisArgLeuEndPheSerSerGlnIleGlnThrGlu  -
  b:  GlyMetIleTrpGlyAspGlyAsnThrAspTyrAsnSerAlaLeuLysSerArgLeuSer -
  c:   GluEndPheGlyValMetGluThrGlnThrIleIleGlnLeuSerAsnProAspEndAla -

CATCAGCAAGGACAACTCCAAGAGCCAAGTTTTCTTAAAAATGAACAGTCTGCACACTGA
541  ---------+---------+---------+---------+---------+---------+ 600
     GTAGTCGTTCCTGTTGAGGTTCTCGGTTCAAAAGAATTTTTACTTGTCAGACGTGTGACT a: HisGlnGlnGlyGlnLeuGlnGluProSerPheLeuLysAsnGluGlnSerAlaHisEnd  -
  b:  IleSerLysAspAsnSerLysSerGlnValPheLeuLysMetAsnSerLeuHisThrAsp -
  c:   SerAlaArgThrThrProArgAlaLysPheSerEndLysEndThrValCysThrLeuMet -
```

FIG. 1C

```
                                                                S
                                                                t
                                                                y
                                                                I
       TGACACAGCCAGGTACTACTGTGCCAGAGAGAGAGATTATAGGCTTGACTACTGGGGCCA
  601  ---------+---------+---------+---------+---------+---------+ 760
       ACTGTGTCGGTCCATGATGACACGGTCTCTCTCTCTAATATCCGAACTGATGACCCCGGT a: EndHisSerGlnvalleuLeuCysGlnArgGluArgLeuEndAlaEndLeuLeuGlyPro  -
    b:  AspThrAlaArgTyrTyrCysAlaArgGluArgAspTyrArgLeuAspTyrTrpGlyGln -
    c:   ThrGlnProGlyThrThrValProGluArgGluIleIleGlyLeuThrThrGlyAlaLys -

B
                      s
              D       t
              s       E
              a       I
              I       I
       AGGCACCACGGTCACCGTCTCCTCATAATAAGAGCTATGGGAGCTTGCATGCAAATTCTA
  661  ---------+---------+---------+---------+---------+---------+ 720
       TCCGTGGTGCCAGTGGCAGAGGAGTATTATTCTCGATACCCTCGAACGTACGTTTAAGAT a: ArgHisHisGlyHisArgLeuLeuIleIleArgAlaMetGlyAlaCysMetGlnIleLeu  -
    b:  GlyThrThrValThrValSerSerEndEndGluLeuTrpGluLeuAlaCysLysPheTyr -
    c:   AlaProArgSerProSerProHisAsnLysSerTyrGlySerLeuHisAlaAsnSerIle -

TTTCAAGGAGACAGTCATAATGAAATACCTATTGCCTACGGCAGCCGCTGGATTGTTATT
  721  ---------+---------+---------+---------+---------+---------+ 780
       AAAGTTCCTCTGTCAGTATTACTTTATGGATAACGGATGCCGTCGGCGACCTAACAATAA a: PheGlnGlyAspSerHisAsnGluIleProIleAlaTyrGlySerArgTypIleValIle  -
    b:  PheLysGluThrValIleMetLysTyrLeuLeuProThrAlaAlaAlaGlyLeuLeuLeu -
    c:   SerArgArgGlnSerEndEndAsnThrTyrCysLeuargGlnProLeuAspCysTyrTyr -

R
                              S                        l
                              s                        e
                              t                        A
                              I                        I
       ACTCGCTGCCCAACCAGCGATGGCCGACATCGAGCTCACCCAGTCTCCAGCCTCCCTTTC
  781  ---------+---------+---------+---------+---------+---------+ 840
       TGAGCGACGGGTTGGTCGCTACCGGCTGTAGCTCGAGTGGGTCAGAGGTCGGAGGGAAAG a: ThrArgCysProThrSerAspGlyArgHisArgAlaHisProValSerSerLeuProPhe  -
    b:  LeuAlaAlaGlnProAlaMetAlaAspIleGluLeuThrGlnSerProAlaSerLeuSer -
    c:   SerLeuProAsnGlnArgTrpProThrSerSerSerProSerLeuGlnProProPheLeu -

TGCGTCTGTGGGAGAAACTGTCACCATCACATGTCGAGCAAGTGGGAATATTCACAATTA
  841  ---------+---------+---------+---------+---------+---------+ 900
       ACGCAGACACCCTCTTTGACAGTGGTAGTGTACAGCTCGTTCACCCTTATAAGTGTTAAT a: CysValCysGlyArgAsnCysHisHisHisMetSerSerLysTrpGluTyrSerGlnLeu  -
    b:  AlaSerValGlyGluThrValThrIleThrCysArgAlaSerGlyAsnIleHisAsnTyr -
    c:   ArgLeuTrpGluLysLeuSerProSerHisValGluGlnValGlyIlePheThrIleIle -
```

FIG. 1D

```
         TTTAGCATGGTATCAGCAGAAACAGGGAAAATCTCCTCAGCTCCTGGTCTATTATACAAC
 901  ---------+---------+---------+---------+---------+---------+ 960
         AAATCGTACCATAGTCGTCTTTGTCCCTTTTAGAGGAGTCGAGGACCAGATAATATGTTG a:   PheSerMetValSerAlaGluThrGlyLysIleSerSerAlaProGlyLeuLeuTyrAsn    -
  b:     LeuAlaTrpTyrGlnGlnLysGlnGlyLysSerProGlnLeuLeuValTyrTyrThrThr  -
  c:       EndHisGlyIleSerArgAsnArgGluAsnLeuLeuSerSerTrpSerIleIleGlnGln -

AACCTTAGCAGATGGTGTGCCATCAAGGTTCAGTGGCAGTGGATCAGGAACACAATATTC
 961  ---------+---------+---------+---------+---------+---------+ 1020
         TTGGAATCGTCTACCACACGGTAGTTCCAAGTCACCGTCACCTAGTCCTTGTGTTATAAG a:   AsnLeuSerArgTrpCysAlaIleLysValGlnTrpGlnTrpIleArgAsnThrIlePhe    -
  b:     ThrLeuAlaAspGlyValProSerArgPheSerGlySerGlySerGlyThrGlnTyrSer  -
  c:       ProEndGlnMetValCysHisGlnGlySerValAlaValAspGlnGluHisAsnIleLeu -

H
                                                     i
                                                     n
                                                     c
                                                     I
                                                     I
         TCTCAAGATCAACAGCCTGCAACCTGAAGATTTTGGGAGTTATTACTGTCAACATTTTTG
 1021 ---------+---------+---------+---------+---------+---------+ 1080
         AGAGTTCTAGTTGTCGGACGTTGGACTTCTAAAACCCTCAATAATGACAGTTGTAAAAAC a:   SerGlnAspGlnGlnProAlaThrEndArgPheTrpGluLeuLeuLeuSerThrPheLeu    -
  b:     LeuLysIleAsnSerLeuGlnProGluAspPheGlySerTyrTyrCysGlnHisPheTrp  -
  c:       SerArgSerThrAlaCysAsnLeuLysIleLeuGlyValIleThrValAsnIlePheGly -

AX
                                          vh
                                          ao
                                          II
                                          /
         GAGTACTCCTCGGACGTTCGGTGGAGGCACCAAGCTCGAGATCAAACGGGAACAAAAACT
 1081 ---------+---------+---------+---------+---------+---------+ 1140
         CTCATGAGGAGCCTGCAAGCCACCTCCGTGGTTCGAGCTCTAGTTTGCCCTTGTTTTTGA a:   GluTyrSerSerAspValArgTrpArgHisGlnAlaArgAspGlnThrGlyThrLysThr    -
  b:     SerThrProArgThrPheGlyGlyGlyThrLysLeuGluIleLysArgGluGlnLysLeu  -
  c:       ValLeuLeuGlyArgSerValGluAlaProSerSerArgSerAsnGlyAsnLysAsnSer -

B
                                       c
                                       l
                                       I
         CATCTCAGAAGAGGATCTGAATTAATAATGATCAAACGGTAATAAGGATCAGCTTGACCT
 1141 ---------+---------+---------+---------+---------+---------+ 1200
         GTAGAGTCTTCTCCTAGACTTAATTATTACTAGTTTGCCATTATTCCTAGTCGAACTGGA a:   HisLeuArgArgGlySerGluLeuIleMetIleLysArgEndEndGlySerAlaEndPro    -
  b:     IleSerGluGluAspLeuAsnEndEndEndSerAsnGlyAsnLysAspGlnLeuAspLeu  -
  c:       SerGlnLysArgIleEndIleAsnAsnAspGlnThrValIleArgIleSerLeuThrCys -
```

FIG. 1E

```
                             A
                             p
                             a
                             B
                             I
       GTGAAGTGAAAAATGGCGCACATTGTGCGACATTTTTTTTGTCTGCCGTTTACCGCTACT
  1201 ---------+---------+---------+---------+---------+---------+ 1260
       CACTTCACTTTTTACCGCGTGTAACACGCTGTAAAAAAAACAGACGGCAAATGGCGATGA a: ValLysEndLysMetAlaHisIleValArgHisPhePheCysLeuProPheThrAlaThr  -
    b:   EndSerGluLysTrpArgThrLeuCysAspIlePhePheValCysArgLeuProLeuLeu -
    c:     GluValLysAsnGlyAlaHisCysAlaThrPhePheLeuSerAlaValTyrArgTyrCys -

B
                     a
                     m
                     H
                     I
       GCGTCACGGATCCCCACGCGCCCTGTAGCGGCGCATTAAGCGCGGCGGGTGTGGTGGTTA
  1261 ---------+---------+---------+---------+---------+---------+ 1320
       CGCAGTGCCTAGGGGTGCGCGGGACATCGCCGCGTAATTCGCGCCGCCCACACCACCAAT a: AlaSerArgIleProThrArgProValAlaAlaHisEndAlaArgArgValTrpTrpLeu  -
    b:   ArgHisGlySerProArgAlaLeuEndArgArgIleLysArgGlyGlyCysGlyGlyTyr -
    c:     ValThrAspProHisAlaProCysSerGlyAlaLeuSerAlaAlaGlyValValValThr -

CGCGCAGCGTGACCGCTACACTTGCCAGCGCCCTAGCGCCCGCTCCTTTCGCTTTCTTCC
  1321 ---------+---------+---------+---------+---------+---------+ 1380
       GCGCGTCGCACTGGCGATGTGAACGGTCGCGGGATCGCGGGCGAGGAAAGCGAAAGAAGG a: ArgAlaAlaEndProLeuHisLeuProAlaProEndArgProLeuLeuSerLeuSerSer  -
    b:   AlaGlnArgAspArgTyrThrCysGlnArgProSerAlaArgSerPheArgPheLeuPro -
    c:     ArgSerValThrAlaThrLeuAlaSerAlaLeuAlaProAlaProPheAlaPhePhePro -

N
                             a
                             e
                             I
       CTTCCTTTCTCGCCACGTTCGCCGGCTTTCCCCGTCAAGCTCTAAATCGGGGGCTCCCTT
  1381 ---------+---------+---------+---------+---------+---------+ 1440
       GAAGGAAAGAGCGGTGCAAGCGGCCGAAAGGGGCAGTTCGAGATTTAGCCCCCGAGGGAA a: LeuProPheSerProArgSerProAlaPheProValLysLeuEndIleGlyGlySerLeu  -
    b:   PheLeuSerArgHisValArgArgLeuSerProSerSerLysSerGlyAlaProPhe    -
    c:     SerPheLeuAlaThrPheAlaGlyPheProArgGlnAlaLeuAsnArgGlyLeuProLeu -

TAGGGTTCCGATTTAGTGCTTTACGGCACCTCGACCCCAAAAAACTTGATTAGGGTGATG
  1441 ---------+---------+---------+---------+---------+---------+ 1500
       ATCCCAAGGCTAAATCACGAAATGCCGTGGAGCTGGGGTTTTTTGAACTAATCCCACTAC a: EndGlySerAspLeuValLeuTyrGlyThrSerThrProLysAsnLeuIleArgValMet  -
    b:   ArgValProIleEndCysPheThrAlaProArgProGlnLysThrEndLeuGlyEndTrp -
    c:     GlyPheArgPheSerAlaLeuArgHisLeuAspProLysLysLeuAspEndGlyAspGly -
```

FIG. 1F

```
              B
              s
              a
              A
              I
        GTTCACGTAGTGGGCCATCGCCCTGATAGACGGTTTTTCGCCCTTTGACGTTGGAGTCCA
1501    ---------+---------+---------+---------+---------+---------+ 1560
        CAAGTGCATCACCCGGTAGCGGGACTATCTGCCAAAAAGCGGGAAACTGCAACCTCAGGT a:   ValHisValValGlyHisArgProAspArgArgPhePheAlaLeuEndArgTrpSerPro   -
   b:     PheThrEndTrpAlaIleAlaLeuIleAspGlyPheSerProPheAspValGlyValHis -
   c:       SerArgSerGlyProSerProEndEndThrValPhrArgProLeuThrLeuGluSerThr -

CGTTCTTTAATAGTGGACTCTTGTTCCAAACTGGAACAACACTCAACCCTATCTCGGTCT
1561    ---------+---------+---------+---------+---------+---------+ 1620
        GCAAGAAATTATCACCTGAGAACAAGGTTTGACCTTGTTGTGAGTTGGGATAGAGCCAGA a:   ArgSerLeuIleValAspSerCysSerLysLeuGluGlnHisSerThrLeuSerArgSer   -
   b:     ValLeuEndEndTrpThrLeuValProAsnTrpAsnAsnThrGlnProTyrLeuGlyLeu -
   c:       PhePheAsnSerGlyLeuLeuPheGlnThrGlyThrThrLeuAsnProIleSerValTyr -

ATTCTTTTGATTTATAAGGGATTTTGCCGATTTCGGCCTATTGGTTAAAAAATGAGCTGA
1621    ---------+---------+---------+---------+---------+---------+ 1680
        TAAGAAAACTAAATATTCCCTAAAACGGCTAAAGCCGGATAACCAATTTTTTACTCGACT a:   IleLeuLeuIleTyrLysGlyPheCysArgPheArgProIleGlyEndLysMetSerEnd   -
   b:     PhePheEndPheIleArgAspPheAlaAspPheGlyLeuLeuValLysLysEndAlaAsp -
   c:       SerPheAspLeuEndGlyIleLeuProIleSerAlaTyrTrpLeuLysAsnGluLeuIle -

TTTAACAAAAATTTAACGCGAATTTTAACAAAATATTAACGTTTACAATTTCAGGTGGCA
1681    ---------+---------+---------+---------+---------+---------+ 1740
        AAATTGTTTTTAAATTGCGCTTAAAATTGTTTTATAATTGCAAATGTTAAAGTCCACCGT a:   PheAsnLysAsnLeuThrArgIleLeuThrLysTyrEndArgLeuGlnPheGlnValAla   -
   b:     LeuThrLysIleEndArgGluPheEndGlnAsnIleAsnValTyrAsnPheArgTrpHis -
   c:       EndGlnLysPheAsnAlaAsnPheAsnLysIleLeuThrPheThrIleSerGlyGlyThr

CTTTTCGGGGAAATGTGCGCGGAACCCCTATTTGTTTATTTTTCTAAATACATTCAAATA
1741    ---------+---------+---------+---------+---------+---------+ 1800
        GAAAAGCCCCTTTACACGCGCCTTGGGGATAAACAAATAAAAAGATTTATGTAAGTTTAT a:   LeuPheGlyGluMetCysAlaGluProLeuPheValTyrPheSerLysTyrIleGlnIle   -
   b:     PheSerGlyLysCysAlaArgAsnProTyrLeuPheIlePheLeuAsnThrPheLysTyr -
   c:       PheArgGlyAsnValArgGlyThrProIleCysLeuPhePheEndIleHisSerAsnMet -

TGTATCCGCTCATGAGACAATAACCCTGATAAATGCTTCAATAATATTGAAAAAGGAAGA
1801    ---------+---------+---------+---------+---------+---------+ 1860
        ACATAGGCGAGTACTCTGTTATTGGGACTATTTACGAAGTTATTATAACTTTTTCCTTCT a:   CysIleArgSerEndAspAsnAsnProAspLysCysPheAsnAsnIleGluLysGlyArg   -
   b:     ValSerAlaHisGluThrIleThrLeuIleAsnAlaSerIleIleLeuLysLysGluGlu -
   c:       TyrProLeuMetArgGlnEndProEndEndMetLeuGlnEndTyrEndLysArgLysSer -
```

FIG. 1G

```
           GTATGAGTATTCAACATTTCCGTGTCGCCCTTATTCCCTTTTTTGCGGCATTTTGCCTTC
    1861   ------------+---------+---------+---------+---------+---------+ 1920
           CATACTCATAAGTTGTAAAGGCACAGCGGGAATAAGGGAAAAAACGCCGTAAAACGGAAG a:     ValEndValPheAsnIleSerValSerProLeuPheProPheLeuArgHisPheAlaPhe  -
    b:      TyrGluTyrSerThrPheProCysArgProTyrSerLeuPheCysGlyIleLeuProSer -
    c:       MetSerIleGlnHisPheArgValAlaLeuIleProPhePheAlaAlaPheCysLeuPro -

CTGTTTTTGCTCACCCAGAAACGCTGGTGAAAGTAAAAGATGCTGAAGATCAGTTGGGTG
    1921   ---------+---------+---------+---------+---------+---------+ 1980
           GACAAAAACGAGTGGGTCTTTGCGACCACTTTCATTTTCTACGACTTCTAGTCAACCCAC a:     LeuPheLeuLeuThrGlnLysArgTrpEndLysEndLysMetLeuLysIleSerTrpVal  -
    b:      CysPheCysSerProArgAsnAlaGlyGluSerLysArgCysEndArgSerValGlyCys -
    c:       ValPheAlaHisProGluThrLeuValLysValLysAspAlaGluAspGlnLeuGlyAla -

CACGAGTGGGTTACATCGAACTGGATCTCAACAGCGGTAAGATCCTTGAGAGTTTTCGCC
    1981   ---------+---------+---------+---------+---------+---------+ 2040
           GTGCTCACCCAATGTAGCTTGACCTAGAGTTGTCGCCATTCTAGGAACTCTCAAAAGCGG a:     HisGluTrpValThrSerAsnTrpIleSerThrAlaValArgSerLeuArgValPheAla  -
    b:      ThrSerGlyLeuHisArgThrGlySerGlnGlnArgEndAspProEndGluPheSerPro -
    c:       ArgValGlyTyrIleGluLeuAspLeuAsnSerGlyLysIleLeuGluSerPheArgPro

X
                          m
                          n
                          I
           CCGAAGAACGTTTTCCAATGATGAGCACTTTTAAAGTTCTGCTATGTGGCGCGGTATTAT
    2041   ---------+---------+---------+---------+---------+---------+ 2100
           GGCTTCTTGCAAAAGGTTACTACTCGTGAAAATTTCAAGACGATACACCGCGCCATAATA a:     ProLysAsnValPheGlnEndEndAlaLeuLeuLysPheCysTyrValAlaArgTyrTyr  -
    b:      ArgArgThrPheSerAsnAspGluHisPheEndSerSerAlaMetTrpArgGlyIleIle -
    c:       GluGluArgPheProMetMetSerThrPheLysValLeuLeuCysGlyAlaValLeuSer -

CCCGTATTGACGCCGGGCAAGAGCAACTCGGTCGCCGCATACACTATTCTCAGAATGACT
    2101   ---------+---------+---------+---------+---------+---------+ 2160
           GGGCATAACTGCGGCCCGTTCTCGTTGAGCCAGCGGCGTATGTGATAAGAGTCTTACTGA a:     ProValLeuThrProGlyLysSerAsnSerValAlaAlaTyrThrIleLeuArgMetThr  -
    b:      ProTyrEndArgArgAlaArgAlaThrArgSerProHisThrLeuPheSerGluEndLeu -
    c:       ArgIleAspAlaGlyGlnGluGlnLeuGlyArgArgIleHisTyrSerGlnAsnAspLeu -

TGGTTGAGTACTCACCAGTCACAGAAAAGCATCTTACGGATGGCATGACAGTAAGAGAAT
    2161   ---------+---------+---------+---------+---------+---------+ 2220
           ACCAACTCATGAGTGGTCAGTGTCTTTTCGTAGAATGCCTACCGTACTGTCATTCTCTTA a:     TrpLeuSerThrHisGlnSerGlnLysSerIleLeuArgMetAlaEndGlnEndGluAsn  -
    b:      GlyEndValLeuThrSerHisArgLysAlaSerTyrGlyTrpHisAspSerLysArgIle -
    c:       ValGluTyrSerProValThrGluLysHisLeuThrAspGlyMetThrValArgGluLeu -

TATGCAGTGCTGCCATAACCATGAGTGATAACACTGCGGCCAACTTACTTCTGACAACGA
    2221   ---------+---------+---------+---------+---------+---------+ 2280
           ATACGTCACGACGGTATTGGTACTCACTATTGTGACGCCGGTTGAATGAAGACTGTTGCT a:     TyrAlaValLeuProEndProEndValIleThrLeuArgProThrTyrPheEndGlnArg  -
    b:      MetGlnCysCysHisAsnHisGluEndEndHisCysGlyGlnLeuThrSerAspAsnAsp -
    c:       CysSerAlaAlaIleThrMetSerAspAsnThrAlaAlaAsnLeuLeuLeuThrThrIle -
```

FIG. 1H

```
       P
       v
       u
       I
       TCGGAGGACCGAAGGAGCTAACCGCTTTTTTGCACAACATGGGGGATCATGTAACTCGCC
2281   ---------+---------+---------+---------+---------+---------+ 2340
       AGCCTCCTGGCTTCCTCGATTGGCGAAAAAACGTGTTGTACCCCCTAGTACATTGAGCGG a:  SerGluAspArgArgSerEndProLeuPheCysThrThrTrpGlyIleMetEndLeuAla  -
   b:    ArgArgThrGluGlyAlaAsnArgPhePheAlaGlnHisGlyGlySerCysAsnSerPro  -
   c:      GlyGlyProLysGluLeuThrAlaPheLeuHisAsnMetGlyAspHisValThrArgLeu -

TTGATCGTTGGGAACCGGAGCTGAATGAAGCCATACCAAACGACGAGCGTGACACCACGA
2341   ---------+---------+---------+---------+---------+---------+ 2400
       AACTAGCAACCCTTGGCCTCGACTTACTTCGGTATGGTTTGCTGCTCGCACTGTGGTGCT a:  LeuIleValGlyAsnArgSerEndMetLysProTyrGlnThrThrSerValThrProArg  -
   b:    EndSerLeuGlyThrGlyAlaGluEndSerHisThrLysArgArgAlaEndHisHisAsp  -
   c:      AspArgTrpGluProGluLeuAsnGluAlaIleProAsnAspGluArgAspThrThrMet -

F
                         s
                         p
                         I
       TGCCTGTAGCAATGGCAACAACGTTGCGCAAACTATTAACTGGCGAACTACTTACTCTAG
2401   ---------+---------+---------+---------+---------+---------+ 2460
       ACGGACATCGTTACCGTTGTTGCAACGCGTTTGATAATTGACCGCTTGATGAATGAGATC a:  CysLeuEndGlnTrpGlnGlnArgCysAlaAsnTyrEndLeuAlaAsnTyrLeuLeuEnd  -
   b:    AlaCysSerAsnGlyAsnAsnValAlaGlnThrIleAsnTrpArgThrThrTyrSerSer  -
   c:      ProValAlaMetAlaThrThrLeuArgLysLeuLeuThrGlyGluLeuLeuThrLeuAla -

CTTCCCGGCAACAATTAATAGACTGGATGGAGGCGGATAAAGTTGCAGGACCACTTCTGC
2461   ---------+---------+---------+---------+---------+---------+ 2520
       GAAGGGCCGTTGTTAATTATCTGACCTACCTCCGCCTATTTCAACGTCCTGGTGAAGACG a:  LeuProGlyAsnAsnEndEndThrGlyTrpArgArgIleLysLeuGlnAspHisPheCys  -
   b:    PheProAlaThrIleAsnArgLeuAspGlyGlyGlyEndSerCysArgThrThrSerAla  -
   c:      SerArgGlnGlnLeuIleAspTrpMetGluAlaAspLysValAlaGlyProLeuLeuArg -

B
                  g
                  l
                  I
       GCTCGGCCCTTCCGGCTGGCTGGTTTATTGCTGATAAATCTGGAGCCGGTGAGCGTGGGT
2521   ---------+---------+---------+---------+---------+---------+ 2580
       CGAGCCGGGAAGGCCGACCGACCAAATAACGACTATTTAGACCTCGGCCACTCGCACCCA a:  AlaArgProPheArgLeuAlaGlyLeuLeuLeuIleAsnLeuGluProValSerValGly  -
   b:    LeuGlyProSerGlyTrpLeuValTyrCysEndEndIleTrpSerArgEndAlaTrpVal  -
   c:      SerAlaLeuProAlaGlyTrpPheIleAlaAspLysSerGlyAlaGlyGluArgGlySer -
```

FIG. 1I

```
                                              P
                                              f
                                              l
                                              1
           B                                  1
           s                                  0
           a                                  8
           I                                  I
      CTCGCGGTATCATTGCAGCACTGGGGCCAGATGGTAAGCCCTCCCGTATCGTAGTTATCT
2581  ---------+---------+---------+---------+---------+---------+ 2640
      GAGCGCCATAGTAACGTCGTGACCCCGGTCTACCATTCGGGAGGGCATAGCATCAATAGA a:   LeuAlaValSerLeuGlnHisTrpGlyGlnMetValSerProProValSerEndLeuSer   -
 b:     SerArgTyrHisCysSerThrGlyAlaArgTrpEndAlaLeuProTyrArgSerTyrLeu -
 c:       ArgGlyIleIleAlaAlaLeuGlyProAspGlyLysProSerArgIleValValIleTyr -

E
                   a
                   m
                   1
                   1
                   0
                   5
                   I
      ACACGACGGGGAGTCAGGCAACTATGGATGAACGAAATAGACAGATCGCTGAGATAGGTG
2641  ---------+---------+---------+---------+---------+---------+ 2700
      TGTGCTGCCCCTCAGTCCGTTGATACCTACTTGCTTTATCTGTCTAGCGACTCTATCCAC a:   ThrArgArgGlyValArgGlnLeuTrpMetAsnGluIleAspArgSerLeuArgEndVal   -
 b:     HisAspGlyGluSerGlyAsnTyrGlyEndThrLysEndThrAspArgEndAspArgCys -
 c:       ThrThrGlySerGlnAlaThrMetAspGluArgAsnArgGlnIleAlaGluIleGlyAla -

CCTCACTGATTAAGCATTGGTAACTGTCAGACCAAGTTTACTCATATATACTTTAGATTG
2701  ---------+---------+---------+---------+---------+---------+ 2760
      GGAGTGACTAATTCGTAACCATTGACAGTCTGGTTCAAATGAGTATATATGAAATCTAAC a:   ProHisEndLeuSerIleGlyAsnCysGlnThrLysPheThrHisIleTyrPheArgLeu   -
 b:     LeuThrAspEndAlaLeuValThrValArgProSerLeuLeuIleTyrThrLeuAspEnd -
 c:       SerLeuIleLysHisTrpEndLeuSerAspGlnValTyrSerTyrIleLeuEndIleAsp -

ATTTAAAACTTCATTTTTAATTTAAAAGGATCTAGGTGAAGATCCTTTTTGATAATCTCA
2761  ---------+---------+---------+---------+---------+---------+ 2820
      TAAATTTTGAAGTAAAAATTAAATTTTCCTAGATCCACTTCTAGGAAAAACTATTAGAGT a:   IleEndAsnPheIlePheAsnLeuLysGlySerArgEndArgSerPheLeuIleIleSer   -
 b:     PheLysThrSerPheLeuIleEndLysAspLeuGlyGluAspProPheEndEndSerHis -
 c:       LeuLysLeuHisPheEndPheLysArgIleEndValLysIleLeuPheAspAsnLeuMet -

TGACCAAAATCCCTTAACGTGAGTTTTCGTTCCACTGAGCGTCAGACCCCGTAGAAAAGA
2821  ---------+---------+---------+---------+---------+---------+ 2880
      ACTGGTTTTAGGGAATTGCACTCAAAAGCAAGGTGACTCGCAGTCTGGGGCATCTTTTCT a:   EndProLysSerLeuAsnValSerPheArgSerThrGluArgGlnThrProEndLysArg   -
 b:     AspGlnAsnProLeuThrEndValPheValProLeuSerValArgProArgArgLysAsp -
 c:       ThrLysIleProEndArgGluPheSerPheHisEndAlaSerAspProValGluLysIle -
```

FIG. 1J

```
        TCAAAGGATCTTCTTGAGATCCTTTTTTTCTGCGCGTAATCTGCTGCTTGCAAACAAAAA
 2881   ---------+---------+---------+---------+---------+---------+ 2940
        AGTTTCCTAGAAGAACTCTAGGAAAAAAAGACGCGCATTAGACGACGAACGTTTGTTTTT a:   SerLysAspLeuLeuGluIleLeuPhePheCysAlaEndSerAlaAlaCysLysGlnLys    -
   b:     GlnArgIlePheLeuArgSerPhePheSerAlaArgAsnLeuLeuLeuAlaAsnLysLys  -
   c:       LysGlySerSerEndAspProPhePheLeuArgValIleCysCysLeuGlnThrLysLys -

AACCACCGCTACCAGCGGTGGTTTGTTTGCCGGATCAAGAGCTACCAACTCTTTTTCCGA
 2941   ---------+---------+---------+---------+---------+---------+ 3000
        TTGGTGGCGATGGTCGCCACCAAACAAACGGCCTAGTTCTCGATGGTTGAGAAAAAGGCT a:   AsnHisArgTyrGlnArgTrpPheValCysArgIleLysSerTyrGlnLeuPhePheArg    -
   b:     ThrThrAlaThrSerGlyGlyLeuPheAlaGlySerArgAlaThrAsnSerPheSerGlu  -
   c:       ProProLeuProAlaValValCysLeuProAspGlnGluLeuProThrLeuPheProLys -

AGGTAACTGGCTTCAGCAGAGCGCAGATACCAAATACTGTCCTTCTAGTGTAGCCGTAGT
 3001   ---------+---------+---------+---------+---------+---------+ 3060
        TCCATTGACCGAAGTCGTCTCGCGTCTATGGTTTATGACAGGAAGATCACATCGGCATCA a:   ArgEndLeuAlaSerAlaGluArgArgTyrGlnIleLeuSerPheEndCysSerArgSer    -
   b:     GlyAsnTrpLeuGlnGlnSerAlaAspThrLysTyrCysProSerSerValAlaValVal  -
   c:       ValThrGlyPheSerArgAlaGlnIleProAsnThrValLeuLeuValEndProEndLeu -

TAGGCCACCACTTCAAGAACTCTGTAGCACCGCCTACATACCTCGCTCTGCTAATCCTGT
 3061   ---------+---------+---------+---------+---------+---------+ 3120
        ATCCGGTGGTGAAGTTCTTGAGACATCGTGGCGGATGTATGGAGCGAGACGATTAGGACA a:   EndAlaThrThrSerArgThrLeuEndHisArgLeuHisThrSerLeuCysEndSerCys    -
   b:     ArgProProLeuGlnGluLeuCysSerThrAlaTyrIleProArgSerAlaAsnProVal  -
   c:       GlyHisHisPheLysAsnSerValAlaProProThrTyrLeuAlaLeuLeuIleLeuLeu -

TACCAGTGGCTGCTGCCAGTGGCGATAAGTCGTGTCTTACCGGGTTGGACTCAAGACGAT
 3121   ---------+---------+---------+---------+---------+---------+ 3180
        ATGGTCACCGACGACGGTCACCGCTATTCAGCACAGAATGGCCCAACCTGAGTTCTGCTA a:   TyrGlnTrpLeuLeuProValAlaIleSerArgValLeuProGlyTrpThrGlnAspAsp    -
   b:     ThrSerGlyCysCysGlnTrpArgEndValValSerTyrArgValGlyLeuLysThrIle  -
   c:       ProValAlaAlaAlaSerGlyAspLysSerCysLeuThrGlyLeuAspSerArgArgEnd

AGTTACCGGATAAGGCGCAGCGGTCGGGCTGAACGGGGGGTTCGTGCACACAGCCCAGCT
 3181   ---------+---------+---------+---------+---------+---------+ 3240
        TCAATGGCCTATTCCGCGTCGCCAGCCCGACTTGCCCCCCAAGCACGTGTGTCGGGTCGA a:   SerTyrArgIleArgArgSerGlyArgAlaGluArgGlyValArgAlaHisSerProAla    -
   b:     ValThrGlyEndGlyAlaAlaValGlyLeuAsnGlyGlyPheValHisThrAlaGlnLeu  -
   c:       LeuProAspLysAlaGlnArgSerGlyEndThrGlyGlySerCysThrGlnProSerLeu -

TGGAGCGAACGACCTACACCGAACTGAGATACCTACAGCGTGAGCTATGAGAAAGCGCCA
 3241   ---------+---------+---------+---------+---------+---------+ 3300
        ACCTCGCTTGCTGGATGTGGCTTGACTCTATGGATGTCGCACTCGATACTCTTTCGCGGT a:   TrpSerGluArgProThrProAsnEndAspThrTyrSerValserTyrGluLysAlaPro    -
   b:     GlyAlaAsnAspLeuHisArgThrGluIleProThrAlaEndAlaMetArgLysArgHis  -
   c:       GluArgThrThrTyrThrGluLeuArgTyrLeuGlnArgGluLeuEndGluSerAlaThr -
```

FIG. 1K

```
       CGCTTCCCGAAGGGAGAAAGGCGGACAGGTATCCGGTAAGCGGCAGGGTCGGAACAGGAG
3301   ---------+---------+---------+---------+---------+---------+ 3360
       GCGAAGGGCTTCCCTCTTTCCGCCTGTCCATAGGCCATTCGCCGTCCCAGCCTTGTCCTC a:     ArgPheProLysGlyGluArgArgThrGlyIleArgEndAlaAlaGlySerGluGlnGlu   -
b:       AlaSerArgArgGluLysGlyGlyGlnValSerGlyLysArgGlnGlyArgAsnArgArg -
c:         LeuProGluGlyArgLysAlaAspArgTyrProValSerGlyArgValGlyThrGlyGlu -

AGCGCACGAGGGAGCTTCCAGGGGGAAACGCCTGGTATCTTTATAGTCCTGTCGGGTTTC
3361   ---------+---------+---------+---------+---------+---------+ 3420
       TCGCGTGCTCCCTCGAAGGTCCCCCTTTGCGGACCATAGAAATATCAGGACAGCCCAAAG a:     SerAlaArgGlySerPheGlnGlyGluThrProGlyIlePheIleValLeuSerGlyPhe   -
b:       AlaHisGluGlyAlaSerArgGlyLysArgLeuValSerLeuEndSerCysArgValSer -
c:         ArgThrArgGluLeuProGlyGlyAsnAlaTrpTyrLeuTyrSerProValGlyPheArg -

GCCACCTCTGACTTGAGCGTCGATTTTTGTGATGCTCGTCAGGGGGGCGGAGCCTATGGA
3421   ---------+---------+---------+---------+---------+---------+ 3480
       CGGTGGAGACTGAACTCGCAGCTAAAAACACTACGAGCAGTCCCCCCGCCTCGGATACCT a:     AlaThrSerAspLeuSerValAspPheCysAspAlaArgGlnGlyGlyGlyAlaTyrGly  -
b:       ProProLeuThrEndAlaSerIlePheValMetLeuValArgGlyAlaGluProMetGlu -
c:         HisLeuEndLeuGluArgArgPheLeuEndCysSerSerGlyGlyArgSerLeuTrpLys -

AAAACGCCAGCAACGCGGCCTTTTTACGGTTCCTGGCCTTTTGCTGGCCTTTTGCTCACA
3481   ---------+---------+---------+---------+---------+---------+ 3540
       TTTTGCGGTCGTTGCGCCGGAAAAATGCCAAGGACCGGAAAACGACCGGAAAACGAGTGT a:     LysThrProAlaThrArgProPheTyrGlySerTrpProPheAlaGlyLeuLeuLeuThr   -
b:       LysArgGlnGlnArgGlyLeuPheThrValProGlyLeuLeuLeuAlaPheCysSerHis -
c:         AsnAlaSerAsnAlaAlaPheLeuArgPheLeuAlaPheCysTrpProPheAlaHisMet -

TGTTCTTTCCTGCGTTATCCCCTGATTCTGTGGATAACCGTATTACCGCCTTTGAGTGAG
3541   ---------+---------+---------+---------+---------+---------+ 3600
       ACAAGAAAGGACGCAATAGGGGACTAAGACACCTATTGGCATAATGGCGGAAACTCACTC a:     CysSerPheLeuArgTyrProLeuIleLeuTrpIleThrValLeuProProLeuSerGlu   -
b:       ValLeuSerCysValIleProEndPheCysGlyEndProTyrTyrArgLeuEndValSer -
c:         PhePheProAlaLeuSerProAspSerValAspAsnArgIleThrAlaPheGluEndAla -

CTGATACCGCTCGCCGCAGCCGAACGACCGAGCGCAGCGAGTCAGTGAGCGAGGAAGCGG
3601   ---------+---------+---------+---------+---------+---------+ 3660
       GACTATGGCGAGCGGCGTCGGCTTGCTGGCTCGCGTCGCTCAGTCACTCGCTCCTTCGCC a:     LeuIleProLeuAlaAlaAlaGluArgProSerAlaAlaSerGlnEndAlaArgLysArg   -
b:       EndTyrArgSerProGlnProAsnAspArgAlaGlnArgValSerGluArgGlySerGly -
c:         AspThrAlaArgArgSerArgThrThrGluArgSerGluSerValSerGluGluAlaGlu -

AAGA
3661   ---- 3664
       TTCT a:     LYS   -
b:       ARG -
c:         -
```

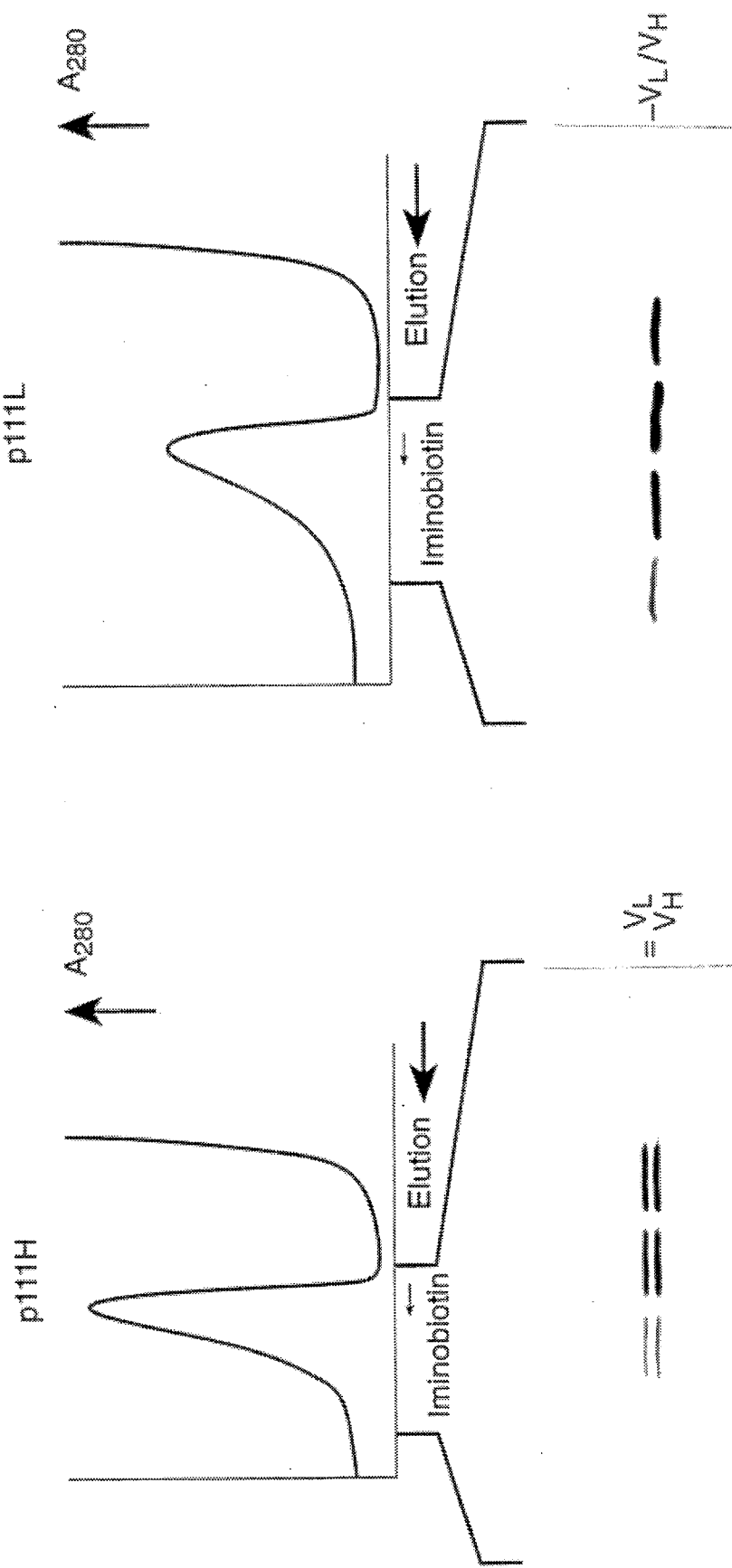

FIG. 8A

```
                P
                f
                l
                M
                I
        ACCCGACACCATCGAATGGCGCAAAACCTTTCGCGGTATGGCATGATAGCGCCCGGAAGA
    1   ---------+---------+---------+---------+---------+---------+  60
        TGGGCTGTGGTAGCTTACCGCGTTTTGGAAAGCGCCATACCGTACTATCGCGGGCCTTCT a:  ThrArgHisHisArgMetAlaGlnAsnLeuSerArgTyrGlyMetIleAlaProGlyArg    -
    b:   ProAspThrIleGluTrpArgLysThrPheArgGlyMetAlaEndEndArgProGluGlu   -
    c:    ProThrProSerAsnGlyAlaLysProPheAlaValTrpHisAspSerAlaArgLysArg  -

GAGTCAATTCAGGGTGGTGAATGTGAAACCAGTAACGTTATACGATGTCGCAGAGTATGC
   61   ---------+---------+---------+---------+---------+---------+ 120
        CTCAGTTAAGTCCCACCACTTACACTTTGGTCATTGCAATATGCTACAGCATCTCATACG a:  GluSerIleGlnGlyGlyGluCysGluThrSerAsnValIleArgCysArgArgValCys   -
    b:   SerGlnPheArgValValAsnValLysProValThrLeuTyrAspValAlaGluTyrAla  -
    c:    ValAsnSerGlyTrpEndMetEndAsnGlnEndArgTyrThrMetSerGlnSerMetPro -

D
                                    r
                                    d
                                    I
                                    I
        CGGTGTCTCTTATCAGACCGTTTCCCGCGTGGTGAACCAGGCCAGCCACGTTTCTGCGAA
  121   ---------+---------+---------+---------+---------+---------+ 180
        GCCACAGAGAATAGTCTGGCAAAGGGCGCACCACTTGGTCCGGTCGGTGCAAAGACGCTT a:  ArgCysLeuLeuSerAspArgPheProArgGlyGluProGlyGlnProArgPheCysGlu   -
    b:   GlyValSerTyrGlnThrValSerArgValValAsnGlnAlaSerHisValSerAlaLys  -
    c:    ValSerLeuIleArgProPheProAlaTrpEndThrArgProAlaThrPheLeuArgLys -

AACGCGGGAAAAAGTGGAAGCGGCGATGGCGGAGCTGAATTACATTCCCAACCGCGTGGC
  181   ---------+---------+---------+---------+---------+---------+ 240
        TTGCGCCCTTTTTCACCTTCGCCGCTACCGCCTCGACTTAATGTAAGGGTTGGCGCACCG a:  AsnAlaGlyLysSerGlySerGlyAspGlyGlyAlaGluLeuHisSerGlnProArgGly   -
    b:   ThrArgGluLysValGluAlaAlaMetAlaGluLeuAsnTyrIleProAsnArgValAla  -
    c:    ArgGlyLysLysTrpLysArgArgTrpArgSerEndIleThrPheProThrAlaTrpHis -

ACAACAACTGGCGGGCAAACAGTCGTTGCTGATTGGCGTTGCCACCTCCAGTCTGGCCCT
  241   ---------+---------+---------+---------+---------+---------+ 300
        TGTTGTTGACCGCCCGTTTGTCAGCAACGACTAACCGCAACGGTGGAGGTCAGACCGGGA a:  ThrThrThrGlyGlyGlnThrValValAlaAspTrpArgCysHisLeuGlnSerGlyPro   -
    b:   GlnGlnLeuAlaGlyLysGlnSerLeuLeuIleGlyValAlaThrSerSerLeuAlaLeu  -
    c:    AsnAsnTrpArgAlaAsnSerArgCysEndLeuAlaLeuProProValTrpProCys    -
```

FIG. 8B

```
       GCACGCGCCGTCGCAAATTGTCGCGGCGATTAAATCTCGCGCCGATCAACTGGGTGCCAG
301    ---------+---------+---------+---------+---------+---------+ 360
       CGTGCGCGGCAGCGTTTAACAGCGCCGCTAATTTAGAGCGCGGCTAGTTGACCCACGGTC a:     AlaArgAlaValAlaAsnCysArgGlyAspEndIleSerArgArgSerThrGlyCysGln  -
b:      HisAlaProSerGlnIleValAlaAlaIleLysSerArgAlaAspGlnLeuGlyAlaSer -
c:       ThrArgArgArgLysLeuSerArgArgLeuAsnLeuAlaProIleAsnTrpValProAla -

CGTGGTGGTGTCGATGGTAGAACGAAGCGGCGTCGAAGCCTGTAAAGCGGCGGTGCACAA
361    ---------+---------+---------+---------+---------+---------+ 420
       GCACCACCACAGCTACCATCTTGCTTCGCCGCAGCTTCGGACATTTCGCCGCCACGTGTT a:     ArgGlyGlyValAspGlyArgThrLysArgArgArgSerLeuEndSerGlyGlyAlaGln  -
b:      ValValValSerMetValGluArgSerGlyValGluAlaCysLysAlaAlaValHisAsn -
c:       TrpTrpCysArgTrpEndAsnGluAlaAlaSerLysProValLysArgArgCysThrIle -
```

```
              A
              f
              lM              B
              Il              c
              Iu              l
              II              I
              /
       TCTTCTCGCGCAACGCGTCAGTGGGCTGATCATTAACTATCCGCTGGATGACCAGGATGC
421    ---------+---------+---------+---------+---------+---------+ 480
       AGAAGAGCGCGTTGCGCAGTCACCCGACTAGTAATTGATAGGCGACCTACTGGTCCTACG a:     SerSerArgAlaThrArgGlnTrpAlaAspHisEndLeuSerAlaGlyEndProGlyCys  -
b:      LeuLeuAlaGlnArgValSerGlyLeuIleIleAsnTyrProLeuAspAspGlnAspAla -
c:       PheSerArgAsnAlaSerValGlyEndSerLeuThrIleArgTrpMetThrArgMetPro -

CATTGCTGTGGAAGCTGCCTGCACTAATGTTCCGGCGTTATTTCTTGATGTCTCTGACCA
481    ---------+---------+---------+---------+---------+---------+ 540
       GTAACGACACCTTCGACGGACGTGATTACAAGGCCGCAATAAAGAACTACAGAGACTGGT a:     HisCysCysGlySerCysLeuHisEndCysSerGlyValIleSerEndCysLeuEndPro  -
b:      IleAlaValGluAlaAlaCysThrAsnValProAlaLeuPheLeuAspValSerAspGln -
c:       LeuLeuTrpLysLeuProAlaLeuMetPheArgArgTyrPheLeuMetSerLeuThrArg -

GACACCCATCAACAGTATTATTTTCTCCCATGAAGACGGTACGCGACTGGGCGTGGAGCA
541    ---------+---------+---------+---------+---------+---------+ 600
       CTGTGGGTAGTTGTCATAATAAAAGAGGGTACTTCTGCCATGCGCTGACCCGCACCTCGT a:     AspThrHisGlnGlnTyrTyrPheLeuProEndArgArgTyrAlaThrGlyArgGlyAla  -
b:      ThrProIleAsnSerIleIlePheSerHisGluAspGlyThrArgLeuGlyValGluHis -
c:       HisProSerThrValLeuPheSerProMetLysThrValArgAspTrpAlaTrpSerIle -
```

```
                                                 A
                                                 p
                                                 a
                                                 I
       TCTGGTCGCATTGGGTCATCAGCAAATCGCGCTGTTAGCGGGCCCATTAAGTTCTGTCTC
601    ---------+---------+---------+---------+---------+---------+ 660
       AGACCAGCGTAACCCAGTAGTCGTTTAGCGCGACAATCGCCCGGGTAATTCAAGACAGAG a:     SerGlyArgIleGlySerSerAlaAsnArgAlaValSerGlyProIleLysPheCysLeu  -
b:      LeuValAlaLeuGlyHisGlnGlnIleAlaLeuLeuAlaGlyProLeuSerSerValSer -
c:       TrpSerHisTrpValIleSerLysSerArgCysEndArgAlaHisEndValLeuSerArg -
```

FIG. 8C

```
      GGCGCGTCTGCGTCTGGCTGGCTGGCATAAATATCTCACTCGCAATCAAATTCAGCCGAT
661   ---------+---------+---------+---------+---------+---------+  720
      CCGCGCAGACGCAGACCGACCGACCGTATTTATAGAGTGAGCGTTAGTTTAAGTCGGCTA
``` a: GlyAlaSerAlaSerGlyTrpLeuAlaEndIleSerHisSerGlnSerAsnSerAlaAsp -
b: AlaArgLeuArgLeuAlaGlyTrpHisLysTyrLeuThrArgAsnSlnIleGlnProIle -
c: ArgValCysValTrpLeuAlaGlyIleAsnIleSerLeuAlaIleLysPheSerArgEnd -

```
      AGCGGAACGGGAAGGCGACTGGAGTGCCATGTCCGGTTTTCAACAAACCATGCAAATGCT
721   ---------+---------+---------+---------+---------+---------+  780
      TCGCCTTGCCCTTCCGCTGACCTCACGGTACAGGCCAAAAGTTGTTTGGTACGTTTACGA
``` a: SerGlyThrGlyArgArgLeuGluCysHisValArgPheSerThrAsnHisAlaAsnAla -
b: AlaGluArgGluGlyAspTrpSerAlaMetSerGlyPheGlnGlnThrMetGlnMetLeu -
c: ArgAsnGlyLysAlaThrGlyValProCysProValPheAsnLysProCysLysCysEnd -

```
      GAATGAGGGCATCGTTCCCACTGCGATGCTGGTTGCCAACGATCAGATGGCGCTGGGCGC
781   ---------+---------+---------+---------+---------+---------+  840
      CTTACTCCCGTAGCAAGGGTGACGCTACGACCAACGGTTGCTAGTCTACCGCGACCCGCG
``` a: GluEndGlyHisArgSerHisCysAspAlaGlyCysGlnArgSerAspGlyAlaGlyArg -
b: AsnGluGlyIleValProThrAlaMetLeuValAlaAsnAspGlnMetAlaLeuGlyAla -
c: MetArgAlaSerPheProLeuArgCysTrpLeuProThrIleArgTrpArgTrpAlaGln -

```
         B
         s
         s                                        E
         H                                        c
         I                                        o
         I                                        R
                                                  V
      AATGCGCGCCATTACCGAGTCCGGGCTGCGCGTTGGTGCGGATATCTCGGTAGTGGGATA
841   ---------+---------+---------+---------+---------+---------+  900
      TTACGCGCGGTAATGGCTCAGGCCCGACGCGCAACCACGCCTATAGAGCCATCACCCTAT
``` a: AsnAlaArgHisTyrArgValArgAlaAlaArgTrpCysGlyTyrLeuGlySerGlyIle -
b: MetArgAlaIleThrGluSerGlyLeuArgValGlyAlaAspIleSerValValGlyTyr -
c: CysAlaProLeuProSerProGlyCysAlaLeuValArgIleSerArgEndTrpAspThr -

```
                                          H
                                          p
                                          a
                                          I
      CGACGATACCGAAGACAGCTCATGTTATATCCCGCCGTTAACCACCATCAAACAGGATTT
901   ---------+---------+---------+---------+---------+---------+  960
      GCTGCTATGGCTTCTGTCGAGTACAATATAGGGCGGCAATTGGTGGTAGTTTGTCCTAAA
``` a: ArgArgTyrArgArgGlnLeuMetLeuTyrProAlaValAsnHisHisGlnThrGlyPhe -
b: AspAspThrGluAspSerSerCysTyrIleProProLeuThrThrIleLysGlnAspPhe -
c: ThrIleProLysThrAlaHisValIleSerArgArgEndProProSerAsnArgIlePhe -

```
      TCGCCTGCTGGGGCAAACCAGCGTGGACCGCTTGCTGCAACTCTCTCAGGGCCAGGCGGT
961   ---------+---------+---------+---------+---------+---------+  1020
      AGCGGACGACCCCGTTTGGTCGCACCTGGCGAACGACGTTGAGAGAGTCCCGGTCCGCCA
``` a: SerProAlaGlyAlaAsnGlnArgGlyProLeuAlaAlaThrLeuSerGlyProGlyGly -
b: ArgLeuLeuGlyGlnThrSerValAspArgLeuLeuGlnLeuSerGlnGlyGlnAlaVal -
c: AlaCysTrpGlyLysProAlaTrpThrAlaCysCysAsnSerLeuArgAlaArgArgEnd -

FIG. 8D

```
              E
              s                                           N
              p                                           a
              3                                           r
              I                                           I
     GAAGGGCAATCAGCTGTTGCCCGTCTCACTGGTGAAAAGAAAAACCACCCTGGCGCCCAA
1021 ---------+---------+---------+---------+---------+---------+ 1080
     CTTCCCGTTAGTCGACAACGGGCAGAGTGACCACTTTTCTTTTTGGTGGGACCGCGGGTT a: GluGlyGlnSerAlaValAlaArgLeuThrGlyGluLysLysAsnHisProGlyAlaGln  -
  b:  LysGlyAsnGlnLeuLeuProValSerLeuValLysArgLysThrThrLeuAlaProAsn -
  c:   ArgAlaIleSerCysCysProSerHisTrpEndLysGluLysProProTrpArgProIle -

TACGCAAACCGCCTCTCCCCGCGCGTTGGCCGATTCATTAATGCAGCTGGCACGACAGGT
1081 ---------+---------+---------+---------+---------+---------+ 1140
     ATGCGTTTGGCGGAGAGGGGCGCGCAACCGGCTAAGTAATTACGTCGACCGTGCTGTCCA a: TyrAlaAsnArgLeuSerProArgValGlyArgPheIleAsnAlaAlaGlyThrThrGly  -
  b:  ThrGlnThrAlaSerProArgAlaLeuAlaAspSerLeuMetGlnLeuAlaArgGlnVal -
  c:   ArgLysProProLeuProAlaArgTrpProIleHisEndCysSerTrpHisAspArgPhe -

TTCCCGACTGGAAAGCGGGCAGTGAGCGCAACGCAATTAATGTGAGTTAGCTCACTCATT
1141 ---------+---------+---------+---------+---------+---------+ 1200
     AAGGGCTGACCTTTCGCCCGTCACTCGCGTTGCGTTAATTACACTCAATCGAGTGAGTAA a: PheProThrGlyLysArgAlaValSerAlaThrGlnLeuMetEndValSerSerLeuIle  -
  b:  SerArgLeuGluSerGlyGlnEndAlaGlnArgAsnEndCysGluLeuAlaHisSerLeu -
  c:   ProAspTrpLysAlaGlySerGluArgAsnAlaIleAsnValSerEndLeuThrHisEnd -

AGGCACCCCAGGCTTTACACTTTATGCTTCCGGCTCGTATGTTGTGTGGAATTGTGAGCG
1201 ---------+---------+---------+---------+---------+---------+ 1260
     TCCGTGGGGTCCGAAATGTGAAATACGAAGGCCGAGCATACAACACACCTTAACACTCGC a: ArgHisProArgLeuTyrThrLeuCysPheArgLeuValCysCysValGluLeuEndAla  -
  b:  GlyThrProGlyPheThrLeuTyrAlaSerGlySerTyrValValTrpAsnCysGluArg -
  c:   AlaProGlnAlaLeuHisPheMetLeuProAlaArgMetLeuCysGlyIleValSerGly -

X
                                                    b
                                                    a
                                                    I
     GATAACAATTTCACACAGGAAACAGCTATGACCATGATTACCAATTTCTAGATAACGAGG
1261 ---------+---------+---------+---------+---------+---------+ 1320
     CTATTGTTAAAGTGTGTCCTTTGTCGATACTGGTACTAATGGTTAAAGATCTATTGCTCC a: AspAsnAsnPheThrGlnGluThrAlaMetThrMetIleThrAsnPheEndIleThrArg  -
  b:  IleThrIleSerHisArgLysGlnLeuEndProEndLeuArgIleSerArgEndArgGly -
  c:   EndGlnPheHisThrGlyAsnSerTyrAspHisAspTyrGluPheLeuAspAsnGluGly -
```

FIG. 8E

```
                               N
                               r
                               u
                               I
         GCAAAAAATGAAAAAGACAGCTATCGCGATTGCAGTGGCACTGGCTGGTTTCGCTACCGT
    1321 ---------+---------+---------+---------+---------+---------+ 1380
         CGTTTTTTACTTTTTCTGTCGATAGCGCTAACGTCACCGTGACCGACCAAAGCGATGGCA a:   AlaLysAsnGluLysAspSerTyrArgAspCysSerGlyThrGlyTrpPheArgTyrArg   -
    b:    GlnLysMetLysLysThrAlaIleAlaIleAlaValAlaLeuAlaGlyPheAlaThrVal  -
    c:     LysLysEndLysArgGlnLeuSerArgLeuGlnTrpHisTrpLeuValSerLeuProEnd -

E
             B S           c           S      k S       B          
             s t           o           s      p m       a    X    SA
             a u           R           t      n a       m    h    ac
             I I           I           I      I I       H    O    lc
                                                        I         II
         AGCGCAGGCCTGAGACCAGAATTCGAGCTCGGTACCCGGGGATCCCTCGAGGTCGACCTG
    1381 ---------+---------+---------+---------+---------+---------+ 1440
         TCGCGTCCGGACTCTGGTCTTAAGCTCGAGCCATGGGCCCCTAGGGAGCTCCAGCTGGAC a:   SerAlaGlyLeuArgProGluPheGluLeuGlyThrArgGlySerLeuGluValAspLeu   -
    b:    AlaGlnAlaEndAspGlnAsnSerSerSerValProGlyAspProSerArgSerThrCys  -
    c:     ArgArgProGluThrArgIleArgAlaArgTyrProGlyIleProArgGlyArgProAla -

S     E
            s     c
            e     o                                     H
            8 B   4                                     i
           P3 s   7                                     n
           s8 p   I                                     d
           t7 M   I                                     I
           II I   I                                     I
            /
         CAGGCAGCGCTTGGCGTCACCCGCAGTTCGGTGGTTAATAAGCTTGACCTGTGAAGTGAA
    1441 ---------+---------+---------+---------+---------+---------+ 1500
         GTCCGTCGCGAACCGCAGTGGGCGTCAAGCCACCAATTATTCGAACTGGACACTTCACTT a:   GlnAlaAlaLeuGlyValThrArgSerSerValValAsnLysLeuAspLeuEndSerGlu   -
    b:    ArgGlnArgLeuAlaSerProAlaValArgTrpLeuIleSerLeuThrCysGluValLys  -
    c:     GlySerAlaTrpArgHisProGlnPheGlyGlyEndEndAlaEndProValLysEndLys -

AAATGGCGCACATTGTGCGACATTTTTTTTGTCTGCCGTTTACCGCTACTGCGTCACGGA
    1501 ---------+---------+---------+---------+---------+---------+ 1560
         TTTACCGCGTGTAACACGCTGTAAAAAAAACAGACGGCAAATGGCGATGACGCAGTGCCT a:   LysTrpArgTjrLeuCysAspIlePhePheValCysArgLeuProLeuLeuArgHisGly   -
    b:    AsnGlyAlaHisCysAlaThrPhePheLeuSerAlaValTyrArgTyrCysValThrAsp  -
    c:     MetAlaHisIleValArgHisPhePheCysLeuProPheThrAlaThrAlaSerArgIle -

TCTCCACGCGCCCTGTAGCGGCGCATTAAGCGCGGCGGGTGTGGTGGTTACGCGCAGCGT
    1561 ---------+---------+---------+---------+---------+---------+ 1620
         AGAGGTGCGCGGGACATCGCCGCGTAATTCGCGCCGCCCACACCACCAATGCGCGTCGCA a:   SerProArgAlaLeuEndArgArgIleLysArgGlyGlyCysGlyGlyTyrAlaGlnArg   -
    b:    LeuHisAlaProCysSerGlyAlaLeuSerAlaAlaGlyValValValThrArgSerVal  -
    c:     SerThrArgProValAlaAlaHisEndAlaArgArgValTrpTrpLeuArgAlaAlaEnd -
```

FIG. 8F

```
     GACCGCTACACTTGCCAGCGCCCTAGCGCCCGCTCCTTTCGCTTTCTTCCCTTCCTTTCT
1621 ---------+---------+---------+---------+---------+---------+ 1680
     CTGGCGATGTGAACGGTCGCGGGATCGCGGGCGAGGAAAGCGAAAGAAGGGAAGGAAAGA a: AspArgTyrThrCysGlnArgProSerAlaArgSerPheArgPheLeuProPheLeuSer  -
  b:   ThrAlaThrLeuAlaSerAlaLeuAlaProAlaProPheAlaPhePheProSerPheLeu -
  c:     ProLeuHisLeuProAlaProEndArgProLeuLeuSerLeuSerSerLeuProPheSer -

N
              a
              e
              I
     CGCCACGTTCGCCGGCTTTCCCCGTCAAGCTCTAAATCGGGGGCTCCCTTTAGGGTTCCG
1681 ---------+---------+---------+---------+---------+---------+ 1740
     GCGGTGCAAGCGGCCGAAAGGGGCAGTTCGAGATTTAGCCCCCGAGGGAAATCCCAAGGC a: ArgHisValArgArgLeuSerProSerSerSerLysSerGlyAlaProPheArgValPro  -
  b:   AlaThrPheAlaGlyPheProArgGlnAlaLeuAsnArgGlyLeuProLeuGlyPheArg -
  c:     ProArgSerProAlaPheProValLysLeuEndIleGlyGlySerLeuEndGlySerAsp -

B
                                                            S
                                                            a
                                                            A
                                                            I
     ATTTAGTGCTTTACGGCACCTCGACCCCAAAAAACTTGATTAGGGTGATGGTTCACGTAG
1741 ---------+---------+---------+---------+---------+---------+ 1800
     TAAATCACGAAATGCCGTGGAGCTGGGGTTTTTTGAACTAATCCCACTACCAAGTGCATC a: IleEndCysPheThrAlaProArgProGlnLysThrEndLeuGlyEndTrpPheThrEnd  -
  b:   PheSerAlaLeuArgHisLeuAspProLysLysLeuAspEndGlyAspGlySerArgSer -
  c:     LeuValLeuTyrGlyThrSerThrProLysAsnLeuIleArgValMetValHisValVal -

TGGGCCATCGCCCTGATAGACGGTTTTTCGCCCTTTGACGTTGGAGTCCACGTTCTTTAA
1801 ---------+---------+---------+---------+---------+---------+ 1860
     ACCCGGTAGCGGGACTATCTGCCAAAAAGCGGGAAACTGCAACCTCAGGTGCAAGAAATT a: TrpAlaIleAlaLeuIleAspGlyPheSerProPheAspValGlyValHisValLeuEnd  -
  b:   GlyProSerProEndEndThrValPheArgProLeuThrLeuGluSerThrPhePheAsn -
  c:     GlyHisArgProAspArgArgPhePheAlaLeuEndArgTrpSerProArgSerLeuIle -

TAGTGGACTCTTGTTCCAAACTGGAACAACACTCAACCCTATCTCGGTCTATTCTTTTGA
1861 ---------+---------+---------+---------+---------+---------+ 1920
     ATCACCTGAGAACAAGGTTTGACCTTGTTGTGAGTTGGGATAGAGCCAGATAAGAAAACT a: EndTrpThrLeuValProAsnTrpAsnAsnThrGlnProTyrLeuGlyLeuPhePheEnd  -
  b:   SerGlyLeuLeuPheGlnThrGlyThrThrLeuAsnProIleSerValTyrSerPheAsp -
  c:     ValAspSerCysSerLysLeuGluGlnHisSerThrLeuSerArgSerIleLeuLeuIle -

TTTATAAGGGATTTTGCCGATTTCGGCCTATTGGTTAAAAAATGAGCTGATTTAACAAAA
1921 ---------+---------+---------+---------+---------+---------+ 1980
     AAATATTCCCTAAAACGGCTAAAGCCGGATAACCAATTTTTTACTCGACTAAATTGTTTT a: PheIleArgAspPheAlaAspPheGlyLeuLeuValLysLysEndAlaAspLeuThrLys  -
  b:   LeuEndGlyIleLeuProIleSerAlaTyrTrpLeuLysAsnGluLeuIleEndGlnLys -
  c:     TryLysGlyPheCysArgPheArgProIleGlyEndLysMetSerEndPheAsnLysAsn -
```

FIG. 8G

```
     ATTTAACGCGAATTTTAACAAAATATTAACGTTTACAATTTCAGGTGGCACTTTTCGGGG
1981 ---------+---------+---------+---------+---------+---------+ 2040
     TAAATTGCGCTTAAAATTGTTTTATAATTGCAAATGTTAAAGTCCACCGTGAAAAGCCCC a: IleEndArgGluPheEndGlnAsnIleAsnValTyrAsnPheArgTrpHisPheSerGly   -
  b:  PheAsnAlaAsnPheAsnLysIleLeuThrPheThrIleSerGlyGlyThrPheArgGly  -
  c:   LeuThrArgIleLeuThrLysTyrEndArgLeuGlnPheGlnValAlaLeuPheGlyGlu -

AAATGTGCGCGGAACCCCTATTTGTTTATTTTTCTAAATACATTCAAATATGTATCCGCT
2041 ---------+---------+---------+---------+---------+---------+ 2100
     TTTACACGCGCCTTGGGGATAAACAAATAAAAAGATTTATGTAAGTTTATACATAGGCGA a: LysCysAlaArgAsnProTyrLeuPheIlePheLeuAsnThrPheLysTyrValSerAla   -
  b:  AsnValArgGlyThrProIleCysLeuPhePheEndIleHisSerAsnMetTyrProLeu  -
  c:   MetCysAlaGluProLeuPheValTyrPheSerLysTyrIleGlnIleCysIleArgSer

CATGAGACAATAACCCTGATAAATGCTTCAATAATATTGAAAAAGGAAGAGTATGAGTAT
2101 ---------+---------+---------+---------+---------+---------+ 2160
     GTACTCTGTTATTGGGACTATTTACGAAGTTATTATAACTTTTTCCTTCTCATACTCATA a: HisGluThrIleThrLeuIleAsnAlaSerIleIleLeuLysLysGluGluTyrGluTyr  -
  b:  MetArgGlnEndProEndEndMetLeuGlnEndTyrEndLysArgLysSerMetSerIle  -
  c:   EndAspAsnAsnProAspLysCysPheAsnAsnIleGluLysGlyArgValEndValPhe -

TCAACATTTCCGTGTCGCCCTTATTCCCTTTTTTGCGGCATTTTGCCTTCCTGTTTTTGC
2161 ---------+---------+---------+---------+---------+---------+ 2220
     AGTTGTAAAGGCACAGCGGGAATAAGGGAAAAAACGCCGTAAAACGGAAGGACAAAAACG a: SerThrPheProCysArgProTyrSerLeuPheCysGlyIleLeuProSerCysPheCys   -
  b:  GlnHisPheArgValAlaLeuIleProPhePheAlaAlaPheCysLeuProValPheAla  -
  c:   AsnIleSerValSerProKeuPheProPheLeuArgHisPheAlaPheLeuPheLeuLeu -

TCACCCAGAAACGCTGGTGAAAGTAAAAGATGCTGAAGATCAGTTGGGTGCACGAGTGGG
2221 ---------+---------+---------+---------+---------+---------+ 2280
     AGTGGGTCTTTGCGACCACTTTCATTTTCTACGACTTCTAGTCAACCCACGTGCTCACCC a: SerProArgAsnAlaGlyGluSerLysArgCysEndArgSerValGlyCysThrSerGly   -
  b:  HisProGluThrLeuValLysValLysAspAlaGluAspGlnLeuGlyAlaArgValGly  -
  c:   ThrGlnLysArgTrpEndLysEndLysMetLeuLysIleSerTrpValHisGluTrpVal - x
                                                              m
                                                              n
                                                              I
     TTACATCGAACTGGATCTCAACAGCGGTAAGATCCTTGAGAGTTTTCGCCCCGAAGAACG
2281 ---------+---------+---------+---------+---------+---------+ 2340
     AATGTAGCTTGACCTAGAGTTGTCGCCATTCTAGGAACTCTCAAAAGCGGGGCTTCTTGC a: LeuHisArgThrGlySerGlnGlnArgEndAspProEndGluPheSerProArgArgThr  -
  b:  TyrIleGluLeuAspLeuAsnSerGlyLysIleLeuGluSerPheArgProGluGluArg -
  c:   ThrSerAsnTrpIleSerThrAlaValArgSerLeuArgValPheAlaProLysAsnVal -

TTTTCCAATGATGAGCACTTTTAAAGTTCTGCTATGTGGCGCGGTATTATCCCGTATTGA
2341 ---------+---------+---------+---------+---------+---------+ 2400
     AAAAGGTTACTACTCGTGAAAATTTCAAGACGATACACCGCGCCATAATAGGGCATAACT a: PheSerAsnAspGluHisPheEndSerSerAlaMetTrpArgGlyIleIleProTyrEnd  -
  b:  PheProMetMetSerThrPheLysValLeuLeuCysGlyAlaValLeuSerArgIleAsp -
  c:   PheGlnEndEndAlaLeuLeuLysPheCysTyrValAlaArgTyrTyrProValLeuThr -
```

FIG. 8H

```
                                                                    S
                                                                    c
                                                                    a
                                                                    I
     CGCCGGGCAAGAGCAACTCGGTCGCCGCATACACTATTCTCAGAATGACTTGGTTGAGTA
2401 ---------+---------+---------+---------+---------+---------+ 2460
     GCGGCCCGTTCTCGTTGAGCCAGCGGCGTATGTGATAAGAGTCTTACTGAACCAACTCAT a: ArgArgAlaArgAlaThrArgSerProHisThrLeuPheSerGluEndLeuGlyEndVal    -
  b:  AlaGlyGlnGluGlnLeuGlyArgArgIleHisTyrSerGlnAsnAspLeuValGluTyr   -
  c:   ProGlyLysSerAsnSerValAlaAlaTyrThrIleLeuArgMetThrTrpLeuSerThr  -

CTCACCAGTCACAGAAAAGCATCTTACGGATGGCATGACAGTAAGAGAATTATGCAGTGC
2461 ---------+---------+---------+---------+---------+---------+ 2520
     GAGTGGTCAGTGTCTTTTCGTAGAATGCCTACCGTACTGTCATTCTCTTAATACGTCACG a: LeuThrSerHisArgLysAlaSerTyrGlyTrpHisAspSerLysArgIleMetGlnCys    -
  b:  SerProValThrGluLysHisLeuThrAspGlyMetThrValArgGluLeuCysSerAla   -
  c:   HisGlnSerGlnLysSerIleLeuArgMetAlaEndGlnEndGluAsnTyrAlaValLeu

P
                                                                    v
                                                                    u
                                                                    I
     TGCCATAACCATGAGTGATAACACTGCGGCCAACTTACTTCTGACAACGATCGGAGGACC
2521 ---------+---------+---------+---------+---------+---------+ 2580
     ACGGTATTGGTACTCACTATTGTGACGCCGGTTGAATGAAGACTGTTGCTAGCCTCCTGG a: CysHisAsnHisGluEndEndHisCysGlyGlnLeuThrSerAspAsnAspArgArgThr    -
  b:  AlaIleThrMetSerAspAsnThrAlaAlaAsnLeuLeuLeuThrThrIleGlyGlyPro   -
  c:   ProEndProEndValIleThrLeuArgProThrTyrPheEndGlnArgSerGluAspArg  -

GAAGGAGCTAACCGCTTTTTTGCACAACATGGGGGATCATGTAACTCGCCTTGATCGTTG
2581 ---------+---------+---------+---------+---------+---------+ 2640
     CTTCCTCGATTGGCGAAAAAACGTGTTGTACCCCCTAGTACATTGAGCGGAACTAGCAAC a: GluGlyAlaAsnArgPhePheAlaGlnHisGlyGlySerCysAsnSerProEndSerLeu    -
  b:  LysGluLeuThrAlaPheLeuHisAsnMetGlyAspHisValThrArgLeuAspArgTrp   -
  c:   ArgSerEndProLeuPheCysThrThrTrpGlyIleMetEndLeuAlaLeuIleValGly  -

GGAACCGGAGCTGAATGAAGCCATACCAAACGACGAGCGTGACACCACGATGCCTGTAGC
2641 ---------+---------+---------+---------+---------+---------+ 2700
     CCTTGGCCTCGACTTACTTCGGTATGGTTTGCTGCTCGCACTGTGGTGCTACGGACATCG a: GlyThrGlyAlaGluEndSerHisThrLysArgArgAlaEndHisHisAspAlaCysSer    -
  b:  GluProGluLeuAsnGluAlaIleProAsnAspGluArgAspThrThrMetProValAla   -
  c:   AsnArgSerEndMetLysProTyrGlnThrThrSerValThrProArgCysLeuEndGln  -

F
                                                                    s
                                                                    p
                                                                    I
     AATGGCAACAACGTTGCGCAAACTATTAACTGGCGAACTACTTACTCTAGCTTCCCGGCA
2701 ---------+---------+---------+---------+---------+---------+ 2760
     TTACCGTTGTTGCAACGCGTTTGATAATTGACCGCTTGATGAATGAGATCGAAGGGCCGT a: AsnGlyAsnAsnValAlaGlnThrIleAsnTrpArgThrThrTyrSerSerPheProAla    -
  b:  MetAlaThrThrLeuArgLysLeuLeuThrGlyGluLeuLeuThrLeuAlaSerArgGlu   -
  c:   TrpGlnGlnArgCysAlaAsnTyrEndLeuAlaAsnTyrLeuLeuEndLeuProGlyAsn  -
```

FIG. 8I

```
      ACAATTAATAGACTGGATGGAGGCGGATAAAGTTGCAGGACCACTTCTGCGCTCGGCCCT
2761  ---------+---------+---------+---------+---------+---------+  2820
      TGTTAATTATCTGACCTACCTCCGCCTATTTCAACGTCCTGGTGAAGACGCGAGCCGGGA a:  ThrIleAsnArgLeuAspGlyGlyGlyEndSerCysArgThrThrSerAlaLeuGlyPro  -
  b:   GlnLeuIleAspTrpMetGluAlaAspLysValAlaGlyProLeuLeuArgSerAlaLeu -
  c:    AsnEndEndThrGlyTrpArgArgIleLysLeuGlnAspHisPheCysAlaArgProPhe
```

```
           B
           g
           l
           I
      TCCGGCTGGCTGGTTTATTGCTGATAAATCTGGAGCCGGTGAGCGTGGCTCTCGCGGTAT
2821  ---------+---------+---------+---------+---------+---------+  2880
      AGGCCGACCGACCAAATAACGACTATTTAGACCTCGGCCACTCGCACCGAGAGCGCCATA a:  SerGlyTrpLeuValTyrCysEndEndIleTrpSerArgEndAlaTrpLeuSerArgTyr  -
  b:   ProAlaGlyTrpPheIleAlaAspLysSerGlyAlaGlyGluArgGlySerArgGlyIle -
  c:    ArgLeuAlaGlyLeuLeuLeuIleAsnLeuGluProValSerValAlaLeuAlaValSer -
```

```
                                            P                    E
                                            f                    a
                                            l                    m
                                            l                    l
                                            l                    1
                                            0                    0
                                            8                    5
                                            I                    I
      CATTGCAGCACTGGGGCCAGATGGTAAGCCCTCCCGTATCGTAGTTATCTACACGACGGG
2881  ---------+---------+---------+---------+---------+---------+  2940
      GTAACGTCGTGACCCCGGTCTACCATTCGGGAGGGCATAGCATCAATAGATGTGCTGCCC a:  HisCysSerThrGlyAlaArgTrpEndAlaLeuProTyrArgSerTyrLeuHisAspGly -
  b:   IleAlaAlaLeuGlyProAspGlyLysProSerArgIleValValIleTyrThrThrGly -
  c:    LeuGlnHisTrpGlyGlnMetValSerProProValSerEndLeuSerThrArgArgGly -
```

```
      GAGTCAGGCAACTATGGATGAACGAAATAGACAGATCGCTGAGATAGGTGCCTCACTGAT
2941  ---------+---------+---------+---------+---------+---------+  3000
      CTCAGTCCGTTGATACCTACTTGCTTTATCTGTCTAGCGACTCTATCCACGGACTCACTA a:  GluSerGlyAsnTyrGlyEndThrLysEndThrAspArgEndAspArgCysLeuThrAsp -
  b:   SerGlnAlaThrMetAspGluArgAsnArgGlnIleAlaGluIleGlyAlaSerLeuIle -
  c:    ValArgGlnLeuTrpMetAsnGluIleAspArgSerLeuArgEndValProHisEndLeu -
```

```
      TAAGCATTGGTAACTGTCAGACCAAGTTTACTCATATATACTTTAGATTGATTTAAAACT
3001  ---------+---------+---------+---------+---------+---------+  3060
      ATTCGTAACCATTGACAGTCTGGTTCAAATGAGTATATATGAAATCTAACTAAATTTTGA a:  EndAlaLeuValThrValArgProSerLeuLeuIleTyrThrLeuAspEndPheLysThr -
  b:   LysHisTrpEndLeuSerAspGlnValTyrSerTyrIleLeuEndIleAspLeuLysLeu -
  c:    SerIleGlyAsnCysGlnThrLysPheThrHisIleTyrPheArgLeuIleEndAsnPhe -
```

```
      TCATTTTTAATTTAAAAGGATCTAGGTGAAGATCCTTTTTGATAATCTCATGACCAAAAT
3061  ---------+---------+---------+---------+---------+---------+  3120
      AGTAAAAATTAAATTTTCCTAGATCCACTTCTAGGAAAAACTATTAGAGTACTGGTTTTA a:  SerPheLeuIleEndLysAspLeuGlyGluAspProPheEndEndSerHisAspGlnAsn -
  b:   HisPheEndPheLysArgIleEndValLysIleLeuPheAspAsnLeuMetThrLysIle -
  c:    IlePheAsnLeuLysGlySerArgEndArgSerPheLeuIleIleSerEndProLysSer -
```

FIG. 8J

```
            CCCTTAACGTGAGTTTTCGTTCCACTGAGCGTCAGACCCCGTAGAAAAGATCAAAGGATC
      3121  ---------+---------+---------+---------+---------+---------+ 3180
            GGGAATTGCACTCAAAAGCAAGGTGACTCGCAGTCTGGGGCATCTTTTCTAGTTTCCTAG a:   ProLeuThrEndValPheValProLeuSerValArgProArgArgLysAspGlnArgIle   -
       b:    ProEndArgGluPheSerPheHisEndAlaSerAspProValGluLysIleLysGlySer  -
       c:     LeuAsnValSerPheArgSerThrGluArgGlnThrProEndLysArgSerLysAspLeu -

TTCTTGAGATCCTTTTTTTCTGCGCGTAATCTGCTGCTTGCAAACAAAAAAACCACCGCT
      3181  ---------+---------+---------+---------+---------+---------+ 3240
            AAGAACTCTAGGAAAAAAAGACGCGCATTAGACGACGAACGTTTGTTTTTTTGGTGGCGA a:   PheLeuArgSerPhePheSerAlaArgAsnLeuLeuLeuAlaAsnLysLysThrThrAla  -
       b:    SerEndAspProPhePheLeuArgValIleCysCysLeuGlnThrLysLysProProLeu -
       c:     LeuGluIleLeuPhePheCysAlaEndSerAlaAlaCysLysGlnLysAsnHisArgTyr -

ACCAGCGGTGGTTTGTTTGCCGGATCAAGAGCTACCAACTCTTTTTCCGAAGGTAACTGG
      3241  ---------+---------+---------+---------+---------+---------+ 3300
            TGGTCGCCACCAAACAAACGGCCTAGTTCTCGATGGTTGAGAAAAAGGCTTCCATTGACC a:   ThrSerGlyGlyLeuPheAlaGlySerArgAlaThrAsnSerPheSerGluGlyAsnTrp  -
       b:    ProAlaValValCysLeuProAspGlnGluLeuProThrLeuPheProLysValThrGly -
       c:     GlnArgTrpPheValCysArgIleLysSerTyrGlnLeuPhePheArgArgEndLeuAla -

CTTCAGCAGAGCGCAGATACCAAATACTGTCCTTCTAGTGTAGCCGTAGTTAGGCCACCA
      3301  ---------+---------+---------+---------+---------+---------+ 3360
            GAAGTCGTCTCGCGTCTATGGTTTATGACAGGAAGATCACATCGGCATCAATCCGGTGGT a:   LeuGlnGlnSerAlaAspThrLysTyrCysProSerSerValAlaValValArgProPro -
       b:    PheSerArgAlaGlnIleProAsnThrValLeuLeuValEndProEndLeuGlyHisHis -
       c:     SerAlaGluArgArgTyrGlnIleLeuSerPheEndCysSerArgSerEndAlaThrThr -

A
                                                                       1
                                                                       w
                                                                       N
                                                                       I
            CTTCAAGAACTCTGTAGCACCGCCTACATACCTCGCTCTGCTAATCCTGTTACCAGTGGC
      3361  ---------+---------+---------+---------+---------+---------+ 3420
            GAAGTTCTTGAGACATCGTGGCGGATGTATGGAGCGAGACGATTAGGACAATGGTCACCG a:   LeuGlnGluLeuCysSerThrAlaTyrIleProArgSerAlaAsnProValThrSerGly -
       b:    PheLysAsnSerValAlaProProThrTyrLeuAlaLeuLeuIleLeuLeuProValAla -
       c:     SerArgThrLeuEndHisArgLeuHisThrSerLeuCysEndSerCysTyrGlnTrpLeu -

TGCTGCCAGTGGCGATAAGTCGTGTCTTACCGGGTTGGACTCAAGACGATAGTTACCGGA
      3421  ---------+---------+---------+---------+---------+---------+ 3480
            ACGACGGTCACCGCTATTCAGCACAGAATGGCCCAACCTGAGTTCTGCTATCAATGGCCT a:   CysCysGlnTrpArgEndValValSerTyrArgValGlyLeuLysThrIleValThrGly -
       b:    AlaAlaSerGlyAspLysSerCysLeuThrGlyLeuAspSerArgArgEndLeuProAsp -
       c:     LeuProValAlaIleSerArgValLeuProGlyTrpThrGlnAspAspSerTyrArgIle -
```

FIG. 8K

```
       TAAGGCGCAGCGGTCGGGCTGAACGGGGGGTTCGTGCACACAGCCCAGCTTGGAGCGAAC
 3481  ---------+---------+---------+---------+---------+---------+ 3540
       ATTCCGCGTCGCCAGCCCGACTTGCCCCCCAAGCACGTGTGTCGGGTCGAACCTCGCTTG a:  EndGlyAlaAlaValGlyLeuAsnGlyGlyPheValHisThrAlaGlnLeuGlyAlaAsn   -
   b:   LysAlaGlnArgSerGlyEndThrGlyGlySerCysThrGlnProSerLeuGluArgThr  -
   c:    ArgArgSerGlyArgAlaGluArgGlyValArgAlaHisSerProAlaTrpSerGluArg -

GACCTACACCGAACTGAGATACCTACAGCGTGAGCTATGAGAAAGCGCCACGCTTCCCGA
 3541  ---------+---------+---------+---------+---------+---------+ 3600
       CTGGATGTGGCTTGACTCTATGGATGTCGCACTCGATACTCTTTCGCGGTGCGAAGGGCT a:  AspLeuHisArgThrGluIleProThrAlaEndAlaMetArgLysArgHisAlaSerArg   -
   b:   ThrTyrThrGluLeuArgTyrLeuGlnArgGluLeuEndGluSerAlaThrLeuProGlu  -
   c:    ProThrProAsnEndAspThrTyrSerValSerTyrGluLysAlaProArgPheProLys -

AGGGAGAAAGGCGGACAGGTATCCGGTAAGCGGCAGGGTCGGAACAGGAGAGCGCACGAG
 3601  ---------+---------+---------+---------+---------+---------+ 3660
       TCCCTCTTTCCGCCTGTCCATAGGCCATTCGCCGTCCCAGCCTTGTCCTCTCGCGTGCTC a:  ArgGluLysGlyGlyGlnValSerGlyLysArgGlnGlyArgAsnArgArgAlaHisGlu   -
   b:   GlyArgLysAlaAspArgTyrProValSerGlyArgValGlyThrGlyGluArgThrArg  -
   c:    GlyGluArgArgThrGlyIleArgEndAlaAlaGlySerGluGlnGluSerAlaArgGly -

GGAGCTTCCAGGGGGAAACGCCTGGTATCTTTATAGTCCTGTCGGGTTTCGCCACCTCTG
 3661  ---------+---------+---------+---------+---------+---------+ 3720
       CCTCGAAGGTCCCCCTTTGCGGACCATAGAAATATCAGGACAGCCCAAAGCGGTGGAGAC a:  GlyAlaSerArgGlyLysArgLeuValSerLeuEndSerCysArgValSerProProLeu   -
   b:   GluLeuProGlyGlyAsnAlaTrpTyrLeuTyrSerProValGlyPheArgHisLeuEnd  -
   c:    SerPheGlnGlyGluThrProGlyIlePheIleValLeuSerGlyPheAlaThrSerAsp -

ACTTGAGCGTCGATTTTTGTGATGCTCGTCAGGGGGGCGGAGCCTATGGAAAAACGCCAG
 3721  ---------+---------+---------+---------+---------+---------+ 3780
       TGAACTCGCAGCTAAAAACACTACGAGCAGTCCCCCCGCCTCGGATACCTTTTTGCGGTC a:  ThrEndAlaSerIlePheValMetLeuValArgGlyAlaGluProMetGluLysArgGln   -
   b:   LeuGluArgArgPheLeuEndCysSerSerGlyGlyArgSerLeuTrpLysAsnAlaSer  -
   c:    LeuSerValAspPheCysAspAlaArgGlnGlyGlyGlyAlaTyrGlyLysThrProAla -

CAACGCGGCCTTTTTACGGTTCCTGGCCTTTTGCTGGCCTTTTGCTCACATG
 3781  ---------+---------+---------+---------+---------+-- 3832
       GTTGCGCCGGAAAAATGCCAAGGACCGGAAAACGACCGGAAAACGAGTGTAC a:  GlnArgGlyLeuPheThrValProGlyLeuLeuLeuAlaPheCysSerHis   -
   b:   AsnAlaAlaPheLeuArgPheLeuAlaPheCysTrpProPheAlaHisMet  -
   c:    ThrArgProPheTyrGlySerTrpProPheAlaGlyLeuLeuLeuThr    -
```

FIG. 9

```
        RBS                    XbaI        RBS
CACAGGAAAACAGCTATGACCATGATTACGAATTCTAGATAACGAGGGCAAAAAATGAAAAAGACAGCTATCGCG
     LacZ: MetThrMetIleThrAsnPheEnd        OmpA: MetLysLysThrAlaIleAla

StuI BsaI  EcoRI SstI KpnI SmaI  BamHI
ATTGCAGTGGCACTGGCTGTTTCGCTACCGTAGGCCTGAGACCTGAGACCAGGAATTCGAGCTCGGTACCCGGGGAT
    IleAlaValAlaLeuAlaGlyPheAlaThrValAlaGlnAlaEnd

XhoI SalI PstI  Eco47III                                    HindIII
CCCTCGAGGTCGACCTGCAGGCagcGCTTGGCGTCACCCGCAGTTCGGTGGTTAATAAGCTTGACCTGTGAAGTG
         Strep-tag: SerAlaTrpArgHisProGlnPheGlyGlyEnd
```

FUSION PEPTIDES WITH BINDING ACTIVITY FOR STREPTAVIDIN

DESCRIPTION

The present invention relates to peptides which impart a binding affinity for streptavidin to a protein which is used with such a peptide, to fusion proteins which contain such a peptide as well as to processes for the production of such a recombinant protein by expression of a DNA sequence coding therefor in suitable host cells according to well-known methods.

Whereas systems for an efficient expression of foreign proteins in numerous different host organisms have been widely established, the detection and purification of the recombinant gene product still remains a problem when proteins are produced by genetic engineering. This applies in particular to cases in which the natural protein of interest has not previously been isolated so that it has neither been possible to characterize it with regard to its biochemical properties nor are specific antisera or monoclonal antibodies against the protein available. Recently this situation has frequently arisen due to the development of the polymerase chain reaction (Bloch W. (1991) Biochemistry 30, 2736–2747) since by this means it is often easier to obtain information on a gene coding for the protein than on the purified natural protein itself.

In order to enable the detection of a recombinant gene product in such cases where specific immunological reagents for the protein are not available, short peptide tags have been used which were fused with the recombinant protein on the gene level. Such fusion peptide sequences are recognized by specific antibodies when they are attached to the amino or carboxy terminal end of a protein sequence. Examples of such peptide tags are the Myc-tag (Munro & Pelham (1986) Cell 46, 291–300; Ward et al. (1989) Nature 341, 544–546), the Flag peptide (Hopp et al. (1988) Bio/Technology 6, 1204– 1210), the KT3 epitope peptide (Martin et al. (1990) Cell 63,843–849; Martin et al. (1992) Science 255, 192– 194), an α-tubulin epitope peptide (Skinner et al. (1991) J. Biol. Chem. 266, 14163–14166) and the T7 gene 10-protein peptide tag (Lutz-Freyermuth et al. (1990) Proc. Natl. Acad. Sci. USA 87, 6393–6397) which have been used successfully for the detection and in some cases also for the purification of the recombinant gene product. In addition it was found that in most of the aforementioned examples these short peptide tags, which are normally 3 to 12 amino acids long, do not interfere with the biological function of the protein and therefore do not necessarily have to be cleaved after expression.

Although these fusion peptides are especially suitable for the detection of a protein and are therefore important aids for the optimization of expression yields and for purification protocols, the possibilities of utilizing their intrinsic affinity properties in a purification scheme are limited. The reason for this is that the advantageous properties of the previously described peptides are based on their strong binding to an antibody. As a consequence, when the protein is bound via the peptide tag to an affinity column which supports an immobilized antibody, quite extreme and hence less mild conditions (i.e. unphysiological pH value or chaotropic reagents) must be used to elute the protein again from the column. However, if the recombinant protein has been produced in a functional form, it is desirable to avoid potentially denaturing conditions during the purification. But, in only three of the examples described above (Hopp et al. (1988); Martin et al. (1990); Skinner et al. (1991) supra) has it been shown that the protein peptide fusion can be eluted using milder conditions i.e. for example competitively using the synthetic peptide. However, even in these cases disadvantages remain since the monoclonal antibodies directed towards the peptide tag are either expensive or difficult to obtain in adequate amounts.

The object of the present invention was therefore to develop short peptide sequences which i) can be linked with a recombinant protein without interfering with its function, ii) allow detection with a reagent which is readily available and iii) have binding properties which are easily controllable.

This object is achieved according to the invention by a peptide comprising the amino acid sequence Trp—X—His— Pro—Gln—Phe—Y—Z, in which X represents any desired amino acid and Y and Z either both denote Gly, or Y denotes Glu and Z denotes Arg or Lys. Within the scope of the invention it was found that the stated peptide sequence has a high binding affinity for streptavidin or "core" streptavidin (a proteolytic cleavage product of streptavidin) (Bayer, E. A., Ben-Hur, H., Hiller, Y. and Wilchek, M. (1989) Biochem. J. 259,369–376).

Therefore if the stated sequence is present in a fusion protein, then this fusion protein also has a high affinity for streptavidin. The present invention therefore also concerns a corresponding fusion protein.

In this case the peptide sequence can be present at the carboxy terminal end of the fusion protein, it can, however, also theoretically be located at the amino terminal end or within the amino acid sequence of the protein provided that this is not associated with any negative properties such as e.g. impeding or destroying the biological activity etc.

The protein present in the fusion protein can be a complete protein or a mutant of a protein such as e.g. a deletion mutant or substitution mutant, and finally it is also possible that only that part of a protein which is of interest is linked to the protein according to the invention.

The fusion proteins according to the invention can easily be detected by binding to a conjugate of streptavidin and a label wherein all labels known to a person skilled in the art can be used as the label. Also the remaining procedure for such a protein test can be carried out under conditions familiar to a person skilled in the art.

The invention in addition concerns an expression vector, in particular a bacterial expression vector, which contains a DNA sequence that is capable of being expressed under the control of a suitable promoter and operator and codes for a peptide according to the invention, and said vector has several restriction cleavage sites adjoining this DNA sequence in the 5' direction which enables the introduction of a further DNA sequence which codes for the protein or part of a protein to be expressed.

The expression vector according to the invention enables the DNA sequence of a protein of interest to be placed in a simple manner in front of a DNA sequence for the peptide according to the invention and thus to obtain a fusion protein according to the invention after expression e.g. in *Escherichia coli*. If the DNA sequence for the protein is inserted into the restriction cleavage site in the 5' direction from the peptide sequence, which are conventional measures for a person skilled in the art as are also the other procedural methods in the production of the expression vector according to the invention, then a fusion protein is obtained which has the peptide according to the invention which mediates the streptavidin affinity at the carboxy terminus.

The restriction cleavage site in the expression vector according to the invention does not necessarily have to be directly adjacent to the first or last base of the DNA sequence coding for the peptide. However, it should preferably be located so that the reading frame is not impaired during transcription and a linkage is formed between the peptide and the amino acid sequence of the protein comprising only a few, preferably at most ten, additional amino acids.

The present invention in addition concerns a process for the production of a recombinant protein by expression of a DNA sequence coding therefor in suitable host cells according to well-known methods, in which a DNA sequence which codes for a fusion protein according to the invention is expressed. The advantages of this process are that the presence of the expression product can be easily detected by means of a conjugate of streptavidin and a label or/and the separation for the purification of the desired protein as a fusion protein can be carried out by means of streptavidin affinity chromatography.

As already set forth above, streptavidin as a conjugate with any desired label can be used to detect the presence of the expression product, i.e. the fusion protein, an enzyme label being preferred within the scope of the invention. In addition the well-known methods for the detection of proteins can also be used for this e.g. ELISA, RIA, Western transfer etc.

A further advantage of the process according to the invention is that the expressed fusion protein can be easily purified by affinity chromatography on a column with immobilized streptavidin. The elution can then be advantageously carried out under very mild conditions e.g. by addition of biotin or compounds similar to biotin or also with the aid of streptavidin affinity peptides obtained by peptide synthesis. Within the scope of the present invention elution with biotin is preferred. It is also preferred that for the affinity chromatography a column is used which is packed with a streptavidin-Agarose matrix or alternatively with streptavidin coupled to Eupergit™C.

The above disclosure of the present invention shows the outstanding advantages which are inherent to the peptide according to the invention and to the fusion proteins containing this peptide to the extent that they enable a more rapid and reliable detection of the fusion protein expression product whereby it should be mentioned that streptavidin is a cheap and readily available reagent which can also be obtained in combination with labels such as fluorescence labels or enzyme labels. Moreover the expressed fusion protein has easily controllable binding properties to streptavidin due to the presence of the peptide according to the invention thus enabling a simple purification of the expression product which can also be carried out on a large technical scale.

Using the expression vectors according to the invention, facilitate the expression of a fusion protein according to the invention and such an expression vector can be applied universally to all proteins to be expressed. The peptide according to the invention does not interfere in the fusion protein with the biological activity of the remaining part of the protein and therefore does not necessarily have to be cleaved off before further use. However, should a cleavage be desired for whatever reason, the expression vector according to the invention can be constructed in such a way that it has a further DNA sequence coding for a specific protease cleavage site between the restriction cleavage site for introducing the DNA sequence for the protein and the sequence coding for the peptide. Consequently this would enable a simple cleavage of the peptide sequence after expression and if desired, after purification and detection of the expression product.

The following examples elucidate the invention further in conjunction with the figures:

In this connection

FIGS. 1A to 1K (SEQ ID NO:1) show the DNA sequence of pASK46 as well as the amino acid sequences which it encodes in all three reading frames and details of the singular restriction cleavage sites;

FIGS. 6A-1 and 6A-2 show the elution profiles of the streptavidin affinity chromatography with the periplasmic fractions as in FIG. 5;

FIGS. 6B-1 and 6B-2 show a streptavidin affinity chromatography analogous to FIG. 6A whereas in this case the antigen lysozyme was added to the periplasmic fraction;

FIGS. 8A to 8K (SEQ ID NO:2) show the DNA sequence of pASK60-Strep and the amino acid sequences which it encodes in all three reading frames as well as the singular restriction cleavage sites; and FIG. 9 shows the annotated sequence of the polylinker of pASK60-Strep.

GENERAL TECHNIQUES

A) Genetic engineering methods, reagents

DNA manipulations were carried out according to conventional methods of genetic engineering (Sambrook J., Fritsch, E. F. and Maniatis T. (1989), Molecular Cloning: A Laboratory Manual. Cold Spring Harbor Laboratory Press, Cold Spring Harbor, N.Y.). The strains *Escherichia coli* K12 TG1 (supE, hsdΔ5, thi, Δ(lac-proAB) [F', traD36, proAB, lacI$^q$ZΔM15]) (Gibson, T. J. (1984) Ph.D. Thesis, Cambridge University, England) and *Escherichia coli* K12 JM83 (ara, Δ(lac-pro AB), rpsL (=strA), φ80, LacZΔM15) (Yanisch-Perron, C., Vieira, J. and Messing, J. (1985), Gene 33, 103–119) were used for cloning and expression. Restriction enzymes were obtained from Boehringer Mannheim, New England Biolabs and Gibco BRL, Taq DNA polymerase was obtained from Promega. Restriction digestion and the polyermase chain reaction (PCR) were carried out using the conditions recommended by the manufacturer. A modified procedure according to Kunkel was used for the site-directed mutagenesis (Geisselsoder, J., Witney, F. and Yuckenberg, P. (1987), Biotechniques 5, 786–791). Oligodeoxynucleotide synthesis was carried out using an Applied Biosystems DNA synthesizer. The covalent streptavidin-alkaline phosphatase conjugate was obtained from Amersham and streptavidin-Agarose was obtained from Biomol or Sigma. All these reagents contained core streptavidin, a proteolytically truncated form of the protein (Bayer, E. A., Ben-Hur, H., Hiller, Y. and Wilchek, M. (1989) Biochem. J. 259, 369–376).

B) Plasmid constructions

The plasmid pASK46 used in this study was composed of earlier gene constructs for the expression of the D1.3Fv fragment in *E. coli* (Ward E. S., Güssow, D., Griffith, A. D., Jones, P. T. and Winter, G. (1989) Nature 341, 544–546) and pASK40 (Skerra, A., Pfitzinger, I. and Plückthun, A. (1991) Bio/Technology, 9, 273–278).

Figure 2:
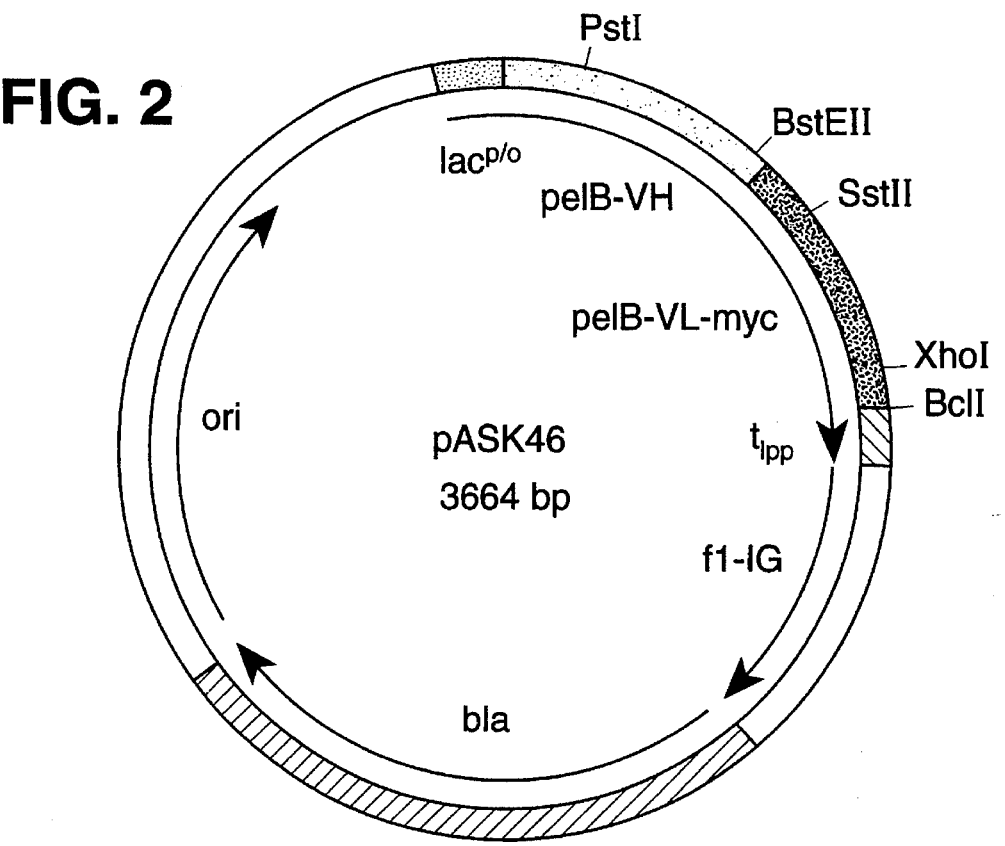
FIG. 2 shows a restriction map of pASK46.
Figure 7:
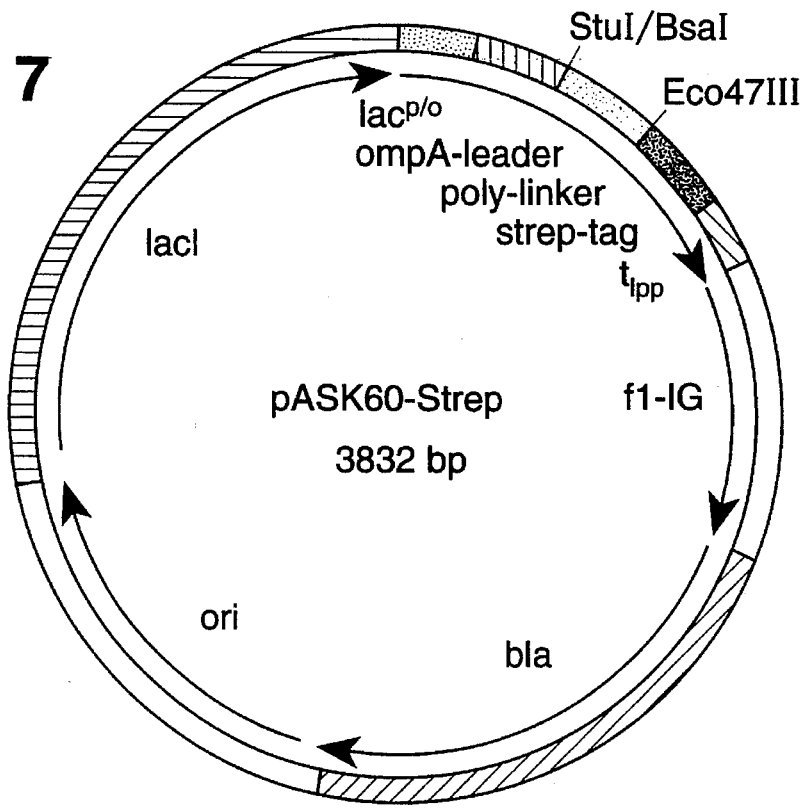
FIG. 7 shows a restriction map of pASK60-Strep.

The complete DNA sequence of pASK46 (SEQ ID NO:1) is shown in FIGS. 1A to 1K. A restriction map of the same plasmid is shown in FIG. 2.

Six derivatives of pASK46 were produced which encode four different peptides at the C-terminus of VH and two peptides at the C-terminus of VL of the D1.3Fv fragment (Boulot, G., Eiselé, J. -L., Bentley, G. A., Bhat, T. N., Ward, E. S., Winter, G. and Poljak, R. J. (1990), J. Mol. Biol., 213, 617–619).

Constructs with peptide tags at VH

The DNA sequence on pASK46 comprising the base pairs 686–706 was replaced by the sequences shown below each of 30 base pairs in length which code for nonapeptides.

```
                          686                      706
                           |                        |
pASK46:         5'-TCCTCA-TAATAAGAGCTATGGGAGCTT-GCATGCAAATTCTA
                   SerSer-EndEnd pASK46-p111H:   5'-TCCTCA-GCGTGGAGGCATCCACAGTTCGGGGGCTAA-GCATGCAAATTCTA
                   SerSer-AlaTrpArgHisProGlnPheGlyGlyEnd pASK46-p141H:   5'-TCCTCA-CAGTGGCTGCATCCACAGTTCGGTGGCTAA-GCATGCAAATTCTA
                   SerSer-GlnTrpLeuHisProGlnPheGlyGlyEnd pASK46-p11XH:   5'-TCCTCA-GCGTGGAGGCATCCACAGTTCGAGCGCTAA-GCATGCAAATTCTA
                   SerSer-AlaTrpArgHisProGlnPheGluArgEnd pASK46-p14XH:   5'-TCCTCA-CAGTGGCTGCATCCACAGTTCGAGCGCTAA-GCATGCAAATTCTA
                   SerSer-GlnTrpLeuHisProGlnPheGluArgEnd
```

Constructs with peptide tags at VL

The DNA sequence on pASK46 comprising the base pairs 1127–1169 was replaced by the sequences shown below of or 44 base pairs in length.

```
                          1127                                          1169
                           |                                             |
pASK46:         5'-ATCAAA-CGGGAACAAAAACTCATCTCAGAAGAGGATCTGAATTAATAA-TGATC
                   IleLys-ArgGluGlnLysLeuIleSerGluGluAspLeuAsnEndEnd pASK46-p111L:   5'-ATCAAA-TCAGCGTGGCGTCATCCACAGTTCGGTGGCTAAGCT-TGATC
                   IleLys-SerAlaTrpArgHisProGlnPheGlyGlyEnd pASK46-p11XL:   5'-ATCAAA-TCAGCGTGGCGTCATCCACAGTTCGAGCGCTAAGCATGCAAGCT-TGATC
                   IleLys-SerAlaTrpArgHisProGlnPheGluArgEnd
```

C) Cell growth, induction and cell lysis

In order to produce the recombinant proteins, *E. coli* cells transformed with the appropriate expression plasmid were incubated at 22° C. in LB medium which contained 100 μg/ml ampicillin until an $OD_{550}$ of 0.5 was achieved. Then IPTG was added at a final concentration of 1 mM, the temperature was reduced if necessary to 20° C. and the induction of the protein expression was continued for 3 hours. The cells were then centrifuged and resuspended in a suitable buffer. For the production of the periplasmic cell fraction, the cells from 1 l culture were resuspended in 10 ml 50 mM Tris pH 8.0, 500 mM sucrose, 1 mM EDTA and incubated for 30 minutes on ice. The spheroplasts were sedimented by centrifugation and the supernatant was sterilized by filtration before further use. If it was intended to purify the preparation with a streptavidin-Agarose column, avidin was added up to a final concentration of 40 μg/ml in order to complex free biotin groups. The protein solution was concentrated by ultrafiltration to a final volume of ca. 1 ml and dialysed overnight against 1 l 50 mM Tris, pH 8.0 at 4° C. Small amounts of precipitate were removed before column chromatography by centrifugation (Microfuge, 14000 rpm, 10 min., 4° C.) or filtration with a Spin-X filtration unit (Costar). In order to prepare the soluble fraction of the total cell protein, the cells from 1 l culture were resuspended in 10 ml 50 mM Tris, pH 8.0 and disrupted with the aid of a high pressure homogenizer (French pressure cell) at 18000 psi. The homogenate was centrifuged (45000 g, 30 min., 4° C.) and avidin was added to the supernatant up to a concentration of 40 μg/ml in order to complex free biotin groups. After a 30 minute incubation at 4° C., the protein solution was sterilized by filtration and applied to the streptavidin-Agarose column. For the SDS-PAGE of the total cell protein, the cells from 4 ml *E. coli* culture were resuspended in 400 μl 50 mM Tris, pH 8.0 and admixed with 100 μl 5×SDS-PAGE application buffer (see below). Chromosomal DNA was fragmented before the gel electrophoresis by ultrasonic treatment.

Example 1

Filter sandwich test

The filter sandwich test was carried out following a strategy which was previously described by Skerra et al. (Skerra, A., Dreher, M. L. and Winter, G. (1991) Anal. Biochem. 196, 151–155). The transformed *E. coli* cells were plated out or spotted on a nitrocellulose filter membrane (82 mm diameter, Schleicher & Schuell) which lay on an agar plate (with LB medium which containing 100 μg/ml ampicillin and 10 mg/ml glucose). The plate was incubated for approximately 8 hours at 37° C. until small colonies were visible. Parallel to this, a second nitrocellulose filter membrane was coated for 6 hours with a solution of 5 mg/ml lysozyme from chicken eggwhite (Sigma) and the antigen of the D1.3 antibody in PBS buffer (4 mM $KH_2PO_4$, 16 mM $Na_2HPO_4$, 115 mM NaCl) and subsequently blocked for two hours in PBS buffer containing 3 % w/v BSA (Sigma, Fraction V) and 0.5 % v/v Tween 20 (Sigma). This "antibody capture membrane" was washed twice with PBS, impregnated with liquid LB medium which contained 100 µg/ml ampicillin and 1 mm IPTG (isopropyl β-D-thiogalactopyranoside, Biomol), placed on an agar plate with the same medium composition and covered with the first membrane carrying the E. coli colonies. The cells on this pile of filters were incubated overnight (14 hours) at room temperature in order to achieve an expression of the Fv fragments with a C-terminal peptide tag. The upper membrane was then lifted and placed on a fresh LB agar plate which contained 100 µg/ml ampicillin and 10 mg/ml glucose in order to store the E. coli colonies at 4° C. for a later proliferation. The "capture" membrane was lifted from the agar and washed three times with PBS/Tween (PBS containing 0.1% v/v Tween). Immobilized Fv fragments which carried peptides with streptavidin binding activity were detected by a 1 hour incubation with a streptavidin-alkaline phosphatase conjugate (diluted 1:2000 in PBS/Tween) in the presence of 2 µg/ml avidin (Polyscience) which had been added 10 minutes beforehand. After thoroughly washing (3×PBS/Tween; 2×PBS), the membrane was incubated in 10 ml AP buffer (100 mM Tris pH 8.8; 100 mM NaCl; 5 mM $MgCl_2$), to which 30 µl BCIP stock solution (50 mg/ml 5-bromo-4-chloro-3-indolyl-phosphate 4-toluidine salt (Biomol) in 30 dimethyl formamide) and 5 µl NBT stock solution (75 mg/ml nitroblue tetrazolium (Biomol) in 70 % v/v dimethyl formamide) had been added (Blake, M. S., Johnston, K. H. Russel-Jones, G. J. and Gotschlich, E. C. (1984) Anal. Biochem., 136, 175–179). The chromogenic reaction was stopped after 30–60 min by washing several times in distilled water and the filter was dried in air.

Figure 3:
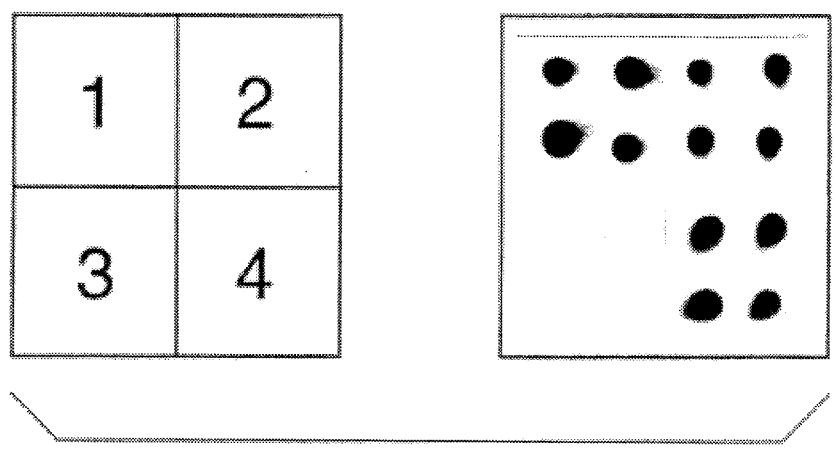
FIG. 3 shows the detection of protein-peptide fusions according to the invention in a filter sandwich test with 4 colonies in each case of *E. coli* transformed with different plasmids.

FIG. 3 shows in each case 4 colonies of Escherichia coli TG1 transformed with the plasmids pASK46-p141H (1), pASK46-p111H (2), pASK46 (3) (as a negative control) and pASK46-p111L (4). Except for the negative control, an intensive binding signal for the streptavidin conjugate is observed in all cases. A somewhat weaker binding signal was detected with the plasmids pASK46-p11XH, pASK46-p11XL and pASK46-p14XH (not shown).

Example 2

SDS-PAGE and Western transfer

SDS-PAGE was carried out in vertical flat gel chambers using the buffer system of Fling, S. P. and Gregerson, D. S. ((1986) Anal. Biochem., 155, 83–88). For the Western transfer, the gel was impregnated in transfer buffer (electrophoretic mobile buffer containing 20 % (v/v) methanol) after electrophoresis. The protein was transferred using the "semi-dry" technique onto an Immobilon-P membrane (Millipore) at a constant current intensity of 1 $mA/cm^2$ during the course of 1 hour at 4° C. The membrane was subsequently blocked with PBS which contained 0.5 % v/v Tween and 3 % BSA w/v for 1 hour at room temperature. After washing three times with PBS/Tween, the membrane was incubated for 10 minutes with avidin (2 µg/ml in PBS/Tween) in order to complex the biotincarboxyl carrier protein. Afterwards it was incubated for 1 hour with a streptavidin-alkaline phosphatase conjugate diluted 1:4000 in PBS/Tween. After thoroughly washing (3×PBS/Tween; 2×PBS), the transfer was developed using the BCIP/NBT protocol (see example 1).

Figure 4:
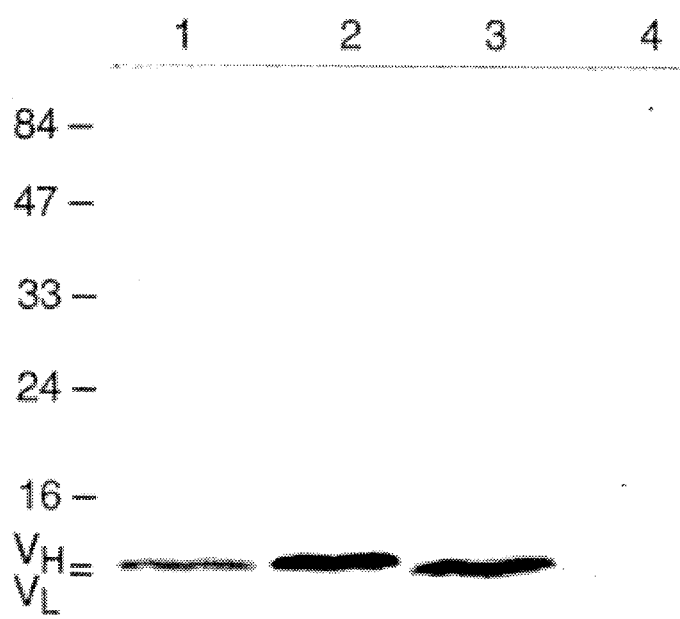
FIG. 4 shows the detection of a protein peptide fusion according to the invention in a Western transfer.

FIG. 4 shows the detection of the corresponding protein-peptide fusions in a Western blot. Identical aliquots of the periplasmic fractions of induced Escherichia coli TG1 cells transformed with the plasmids pASK46-p141H (1), pASK46-p111H (2), pASK46-p111L (3) and pASK46 (4) (as a negative control) were separated by SDS-PAGE. After transfer of the proteins onto an Immobilon-P membrane, the corresponding peptide-protein fusion was specifically detected using the streptavidin conjugate. The plasmids pASK46-p11XH, pASK46-p11XL and pASK46-p14XH (not shown) gave a somewhat weaker signal in an analogous experiment. Comparable results were obtained when the total cell protein was separated in the SDS-PAGE.

Example 3

ELISA

Seven rows of a microtitre plate with 96 wells (Falcon #3912) were coated at 4° C. overnight with 100 µl of a solution of 3 mg/ml lysozyme in 50 mM $NaHCO_3$, pH 9.6. Subsequently they were blocked for 2 hours at room temperature with 2 % w/v fat-free dried milk (BioRad) in PBS. After washing (3×PBS/Tween), 50 µl aliquots of the periplasmic cell fractions of the corresponding clones were added by pipette as serial dilutions in PBS/Tween and incubated for 1 hour. The concentrations of the Fv fragments in the undiluted fractions were approximately 50–100 µg/ml (estimated by SDS-PAGE). After washing (3×PBS/Tween), 50 µl streptavidin-alkaline phosphatase conjugate was added at a dilution of 1:1000 in PBS/Tween and incubated for 1 hour. Unbound conjugate was removed by washing twice in each case with PBS/Tween and PBS, and 100 µl NPP solution (0.5 mg/ml p-nitrophenyl phosphate; 0.9M diethanolamine, pH 9,6; 1 mM $MgCl_2$) was added by pipette. The colour signal was developed for 5–10 minutes and stopped by addition of 100 µl 10 mM EDTA, pH 8.0. The absorbance values were determined using a microtitre plate photometer and the data were plotted as $A_{405}-A_{450}$=differential values after subtracting the blank value for each dilution. The blank values were determined by serial dilutions of the periplasmic cell fraction which contained the D1.3 Fv fragment without a peptide tag and proved to be constant over the entire dilution range ($A_{405}-A_{450}$= 0.199±0.009).

Figure 5:
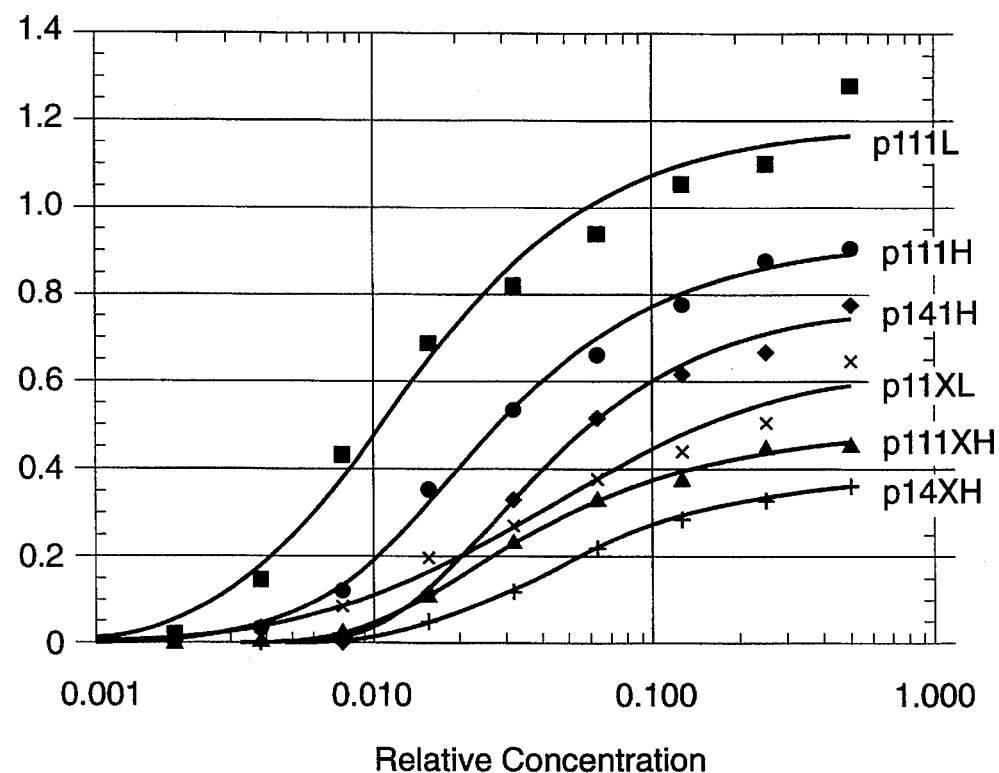
FIG. 5 shows the binding signals observed in an ELISA for a streptavidin conjugate with dilutions of periplasmic fractions from induced *E. coli* TG1 cells transformed with plasmids which code for different fusions according to the invention of an antibody fragment and a streptavidin affinity peptide.

FIG. 5 shows the observed binding signals for the streptavidin conjugate with serial dilutions of the periplasmic fractions of induced Escherichia coli TG1 cells transformed with the corresponding plasmids.

Example 4

Protein purification by streptavidin affinity chromatography.

A column which was packed with 6 ml streptavidin Agarose (about 1 mg streptavidin per 1 ml gel) was equilibrated with 10 volumes of 50 mM Tris, pH 8.0. The periplasmic cell fraction from 0.5 l E. coli cells transformed with the corresponding plasmid was applied to the column and rewashed with the Tris buffer. The hybrid D1.3 Fv fragment was then specifically eluted with a solution of 1 mM iminobiotin (Sigma) or 5 mM lipoic acid (Sigma) in the same buffer. Since these biotin analogues bind much more weakly to streptavidin than biotin itself (Green, N. M. (1975) Adv. Protein Chem., 29, 85–133), it was possible to regenerate the column by simply washing with 10 volumes Tris buffer. All chromatographic steps were carried out at a flow rate of 30 ml/hour at a temperature of 4° C. The streptavidin affinity chromatography of the soluble fraction of the total cell protein was carried out at a flow rate of about 20 ml/hour under otherwise identical conditions. The yield of purified hybrid Fv fragment was normally in the range of 0.5 mg/L·OD$_{550}$ E. coli culture. For the streptavidin affinity chromatography of the D1.3 Fv-lysozyme complex, a periplasmic cell fraction which contained the D1.3 Fv(p111L) fragment and had been dialysed against 50 mM NaH$_2$PO$_4$, pH 7.0, 115 mM NaCl, 1 mM EDTA was admixed with the ca. three-fold molar amount of lysozyme. After 1 hour incubation at 4° C. and subsequent centrifugation, the resulting protein solution was subjected to streptavidin-Agarose affinity chromatography (as above) in which case the last-named buffer was used.

Figures 1, 6B:
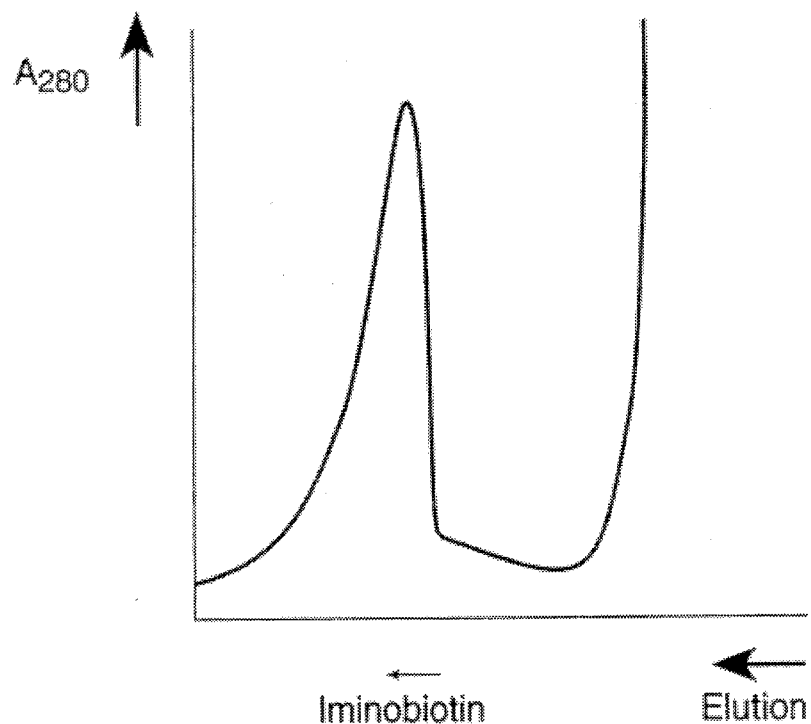
Figures 2, 6B:
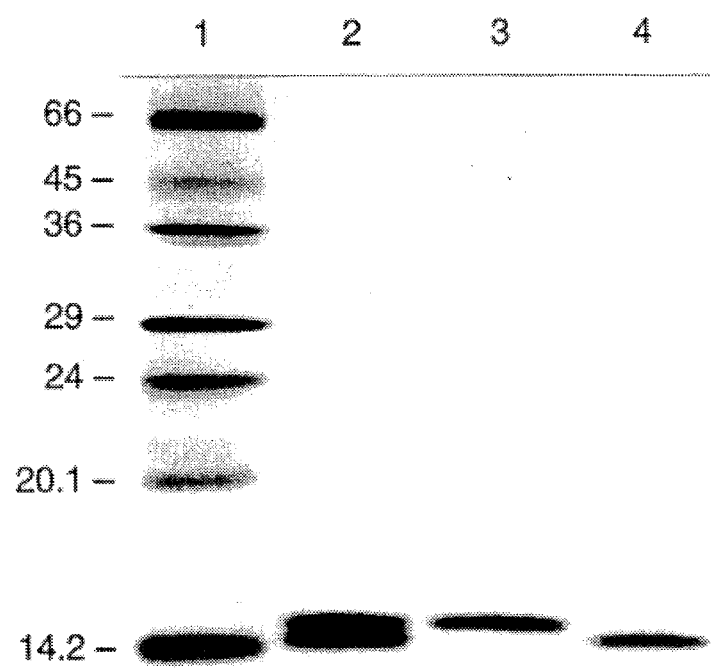

FIGS. 6A-1 and 6A-2 shows the elution profiles (absorbance at 80 nm) of the streptavidin affinity chromatography which was carried out with the periplasmic fractions of *Escherichia coli* TG1 cells which were transformed with pASK46-p111H or pASK46-p111L. Below this the SDS polyacrylamide gels of the fractions obtained after application of an iminobiotin solution stained with Coomassie brilliant blue (Serva) are shown. It can be seen that both subunits of the Fv fragment were eluted together specifically and in a pure form although in each case only one chain of the heterodimeric protein was fused with the streptavidin affinity peptide. In the case of pASK46-p111L both chains had the same mobility in the SDS-PAGE. The functionality of the purified protein was therefore additionally examined by an ELISA experiment (as in example 3). The recombinant protein was also obtained as an intact heterodimer in pure form in a chromatography carried out analogously in which the total cell protein of *Escherichia coli* TG1 cells which were transformed with pASK46-p111H was applied.

FIGS. 6B-1 and 6B-2 shows an analogous streptavidin affinity chromatography in which case lysozyme, the antigen of the D1.3 Fv fragment, had been added to the periplasmic fraction of *Escherichia coli* TG1 cells transformed with pASK46-p111L. The SDS polyacrylamide gel shown under the elution profile which was stained with Coomassie brilliant blue (Serva) shows the product fraction (2) obtained by elution with the iminobiotin solution and in comparison purified lysozyme (3) as well as the recombinant Fv fragment (4) purified separately. Lane (1) shows the molecular weight standard. It can be seen that the immune complex of recombinant Fv fragment and the antigen lysozyme has been specifically purified.

Example 5

Construction and use of pASK60-Strep pASK60-Strep was produced starting with pASK40 (Skerra, A., Pfitzinger, I. and Plückthun, A. (1991) Bio/Technology 9, 273–278) using site-directed mutagenesis and PCR. A restriction map and the total DNA sequence of pASK60-Strep are shown in FIGS. 7 and 8A to 8K. The polylinker on pASK60-Strep contains an improved set of singular restriction cleavage sites, including two restriction cleavage sites which are located directly at the 3' end of the region coding for the OmpA signal peptide, and is followed by a DNA sequence coding for the streptavidin binding peptide "(Ser—Ala—)Trp—Arg—His—Pro—Gln—Phe—Gly—Gly" (cf FIG. 9). The direct expression of a foreign gene in *E. coli*, i.e. without using the OmpA signal sequence, can be achieved by using the XbaI cleavage site and reconstructing the region comprising 16 base pairs between the stop codon of the lacZ mini cistron and the start codon of the structural gene (formerly OmpA signal sequence). On the other hand, in order to produce a fusion with the OmpA signal sequence, which is coded on pASK60-Strep, the structural gene can be cloned directly using the StuI or BsaI cleavage sites. StuI (recognition sequence "AGG CCT") generates a blunt end after the first nucleotide of the last codon (Ala) of the signal sequence. A precise fusion can thus be created directly in front of the structural gene with the aid of a compatible restriction site (e.g. StuI, PvuII, NruI). BsaI is a restriction enzyme of the IIa type, whose cleavage site is far from the recognition site ("GAGACC", underlined in FIG. 9). A 5' overhanging DNA end is generated with this enzyme ("GGCC", printed in small letters in FIG. 9) which is located at the extreme 3' end of the signal sequence without protruding into the coding region of the mature part of the gene to be cloned. This cohesive end can be ligated with the ends that are generated by the restriction enzymes EaeI and EagI. During the preparation of the DNA fragment to be cloned it is also possible to introduce a compatible restriction site e.g. by PCR which does not impair the mature amino terminal coding region of the gene when the BsaI (or another IIa enzyme such as BspMI etc.) recognition sequence is placed on the opposite side of the cohesive end which it is intended to generate. The fusion of the structural gene to the region coding for the streptavidin binding peptide can be achieved using the Eco47III restriction cleavage site (recognition sequence "AGC GCT") which leads to a blunt cut directly between the Ser codon ("AGC", printed in small letters in FIG. 9) and the Ala codon in front of the actual peptide sequence according to claim 1. If it is intended to construct the Ser codon, various restriction sites can be used apart from Eco47III to generate a compatible end, e.g. also ScaI and NruI.

Example 6

Expression and detection of a soluble domain of the LDL receptor using pASK60-Strep The human low density lipoprotein receptor is composed of five protein domains, in addition to a N-terminal signal sequence which is cleaved in the mature receptor, of which the fourth represents the transmembrane part.

In order to clone the first N-terminal protein domain which comprises the amino acids 1 to 292, the plasmid pLDLR3 (ATCC No. 57004) (Yamamoto, T., Davis, C. G., Brown, M. S., Schneider, W. J., Casey, M. L., Goldstein, J. L. and Russell, D. W. (1984) Cell 39, 27–38) was used. The corresponding DNA fragment was amplified by PCR using the oligodeoxynucleotide primer "5'-TAG CAA CGG CCG CAG TGG GCA ACA GAT GT" (for the N-terminus with the restriction cleavage site EagI) and "5'-TTC GTT AGT ACT GCA CTC TTT GAT GGG TTC" (for the C-terminus with the restriction cleavage site ScaI) isolated and cleaved with the restriction enzymes EagI and ScaI. This DNA fragment was cloned into pASK60-Strep via its restriction cleavage sites BsaI and Eco47III using the *E. coli* strain K12 JM83. After checking the plasmid obtained by restriction analysis and DNA sequencing, a culture was prepared from one clone and the protein expression induced as described above. The total cell protein of the cells obtained was separated in a 15% SDS-PAGE and transferred by Western transfer onto an Immobilon P membrane. The recombinant receptor domain of ca. 40000 Daltons could be specifically detected using the streptavidin-alkaline phosphatase conjugate (cf. example 2).

We claim:

1. An isolated peptide comprising the amino acid sequence Trp—X—His—Pro—Gln—Phe—Y—Z, wherein X represents any amino acid residue, and Y and Z both represent Gly or where Y represents Glu, Z represents Arg or Lys.

2. A fusion protein comprising the peptide of claim 1 linked to a protein.

3. A fusion protein of claim 2, wherein said protein is selected from the group consisting of a complete protein, a deletion mutant, a substitution mutant and a portion of a protein.

4. An expression vector comprising a nucleic acid molecule, which codes for the peptide of claim 1, wherein said expression vector has a restriction cleavage site adjoining said nucleic acid molecule in the 5' and 3' direction, which enables the introduction of a further nucleic acid molecule which codes for a protein or a part of a protein which is to be expressed.

5. A method of producing a fusion protein, comprising transfecting a vector having a nucleic acid molecule encoding the fusion protein of claim 2 into a suitable host cell, culturing said host cell under conditions appropriate for expression of said fusion protein, and recovering said fusion protein.

6. A method for detecting the presence of the fusion protein of claim 2 in a sample, comprising contacting said sample with a conjugate of streptavidin and a label to form a complex, further contacting said complex with a reagent and detecting the presence of said fusion protein.

7. The method of claim 6, wherein said label is a fluorescent label.

8. The method of claim 6, wherein said label is an enzyme.

9. Method of claim 8, wherein said enzyme is alkaline phosphatase.

10. The method for isolating a protein linked to the peptide of claim 1, from a sample, comprising subjecting said sample to streptavidin affinity chromatography to form a complex between said peptide and streptavidin, and eluting said protein by contacting said complex with a streptavidin ligand, and isolating the protein from said sample.

11. The method of claim 10, wherein said streptavidin affinity chromatography utilizes a streptavidin-agarose matrix.

12. The method of claim 10, wherein said ligand is a peptide comprising the amino acid sequence Trp—X—His—Pro—Gln—Phe—Y—Z, wherein X represents any amino acid residue, and Y and Z both represent Gly or where Y represents Glu, Z represents Arg or Lys.

13. The method of claim 10, wherein said ligand is biotin or a synthetic derivative thereof.

14. The method of claim 13, wherein said ligand is 2iminobiotin or lipoic acid.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
    ( A ) LENGTH: 3664 bases
    ( B ) TYPE: nucleic acid
    ( C ) STRANDEDNESS: single
    ( D ) TOPOLOGY: linear ( x i ) SEQUENCE DESCRIPTION: SEQ ID NO: 1:

| | | | | | | |
|---|---|---|---|---|---|---|
| GCGCCCAATA | CGCAAACCGC | CTCTCCCCGC | GCGTTGGCCG | ATTCATTAAT | GCAGCTGGCA | 60 |
| CGACAGGTTT | CCCGACTGGA | AAGCGGGCAG | TGAGCGCAAC | GCAATTAATG | TGAGTTAGCT | 120 |
| CACTCATTAG | GCACCCCAGG | CTTTACACTT | TATGCTTCCG | GCTCGTATGT | TGTGTGGAAT | 180 |
| TGTGAGCGGA | TAACAATTTC | ACACAGGAAA | CAGCTATGAC | CATGATTACG | CCAAGCTTGC | 240 |
| ATGCAAATTC | TATTTCAAGG | AGACAGTCAT | AATGAAATAC | CTATTGCCTA | CGGCAGCCGC | 300 |
| TGGATTGTTA | TTACTCGCTG | CCCAACCAGC | GATGGCCCAG | GTGCAGCTGC | AGGAGTCAGG | 360 |
| ACCTGGCCTG | GTGGCGCCCT | CACAGAGCCT | GTCCATCACA | TGCACCGTCT | CAGGGTTCTC | 420 |
| ATTAACCGGC | TATGGTGTAA | ACTGGGTTCG | CCAGCCTCCA | GGAAAGGGTC | TGGAGTGGCT | 480 |
| GGGAATGATT | TGGGGTGATG | GAAACACAGA | CTATAATTCA | GCTCTCAAAT | CCAGACTGAG | 540 |
| CATCAGCAAG | GACAACTCCA | AGAGCAAGT | TTTCTTAAAA | ATGAACAGTC | TGCACACTGA | 600 |
| TGACACAGCC | AGGTACTACT | GTGCCAGAGA | GAGAGATTAT | AGGCTTGACT | ACTGGGGCCA | 660 |
| AGGGACCACG | GTCACCGTCT | CCTCATAATA | AGAGCTATGG | GAGCTTGCAT | GCAAATTCTA | 720 |
| TTTCAAGGAG | ACAGTCATAA | TGAAATACCT | ATTGCCTACG | GCAGCCGCTG | GATTGTTATT | 780 |
| ACTCGCTGCC | CAACCAGCGA | TGGCCGACAT | CGAGCTCACC | CAGTCTCCAG | CCTCCCTTTC | 840 |
| TGCGTCTGTG | GGAGAAACTG | TCACCATCAC | ATGTCGAGCA | AGTGGGAATA | TTCACAATTA | 900 |
| TTTAGCATGG | TATCAGCAGA | AACAGGGAAA | ATCTCCTCAG | CTCCTGGTCT | ATTATACAAC | 960 |
| AACCTTAGCA | GATGGTGTGC | CATCAAGGTT | CAGTGGCAGT | GGATCAGGAA | CACAATATTC | 1020 |
| TCTCAAGATC | AACAGCCTGC | AACCTGAAGA | TTTGGGAGT | TATTACTGTC | AACATTTTTG | 1080 |
| GAGTACTCCT | CGGACGTTCG | GTGGAGGGAC | CAAGCTCGAG | ATCAAACGGG | AACAAAAACT | 1140 |
| CATCTCAGAA | GAGGATCTGA | ATTAATAATG | ATCAAACGGT | AATAAGGATC | AGCTTGACCT | 1200 |
| GTGAAGTGAA | AAATGGCGCA | CATTGTGCGA | CATTTTTTT | GTCTGCCGTT | TACCGCTACT | 1260 |
| GCGTCACGGA | TCCCCACGCG | CCCTGTAGCG | GCGCATTAAG | CGCGGCGGGT | GTGGTGGTTA | 1320 |
| CGCGCAGCGT | GACCGCTACA | CTTGCCAGCG | CCCTAGCGCC | CGCTCCTTTC | GCTTTCTTCC | 1380 |
| CTTCCTTTCT | CGCCACGTTC | GCCGGCTTTC | CCCGTCAAGC | TCTAAATCGG | GGGCTCCCTT | 1440 |
| TAGGGTTCCG | ATTTAGTGCT | TTACGGCACC | TCGACCCCAA | AAAACTTGAT | TAGGGTGATG | 1500 |
| GTTCACGTAG | TGGGCCATCG | CCCTGATAGA | CGGTTTTTCG | CCCTTTGACG | TTGGAGTCCA | 1560 |
| CGTTCTTTAA | TAGTGGACTC | TTGTTCCAAA | CTGGAACAAC | ACTCAACCCT | ATCTCGGTCT | 1620 |
| ATTCTTTTGA | TTTATAAGGG | ATTTTGCCGA | TTTCGGCCTA | TTGGTTAAAA | AATGAGCTGA | 1680 |
| TTTAACAAAA | ATTTAACGCG | AATTTTAACA | AAATATTAAC | GTTACAATT | TCAGGTGGCA | 1740 |
| CTTTTCGGGG | AAATGTGCGC | GGAACCCCTA | TTTGTTTATT | TTTCTAAATA | CATTCAAATA | 1800 |
| TGTATCCGCT | CATGAGACAA | TAACCCTGAT | AAATGCTTCA | ATAATATTGA | AAAAGGAAGA | 1860 |

| | | | | | |
|---|---|---|---|---|---|
| GTATGAGTAT | TCAACATTTC | CGTGTCGCCC | TTATTCCCTT | TTTTGCGGCA | TTTTGCCTTC | 1920
| CTGTTTTTGC | TCACCCAGAA | ACGCTGGTGA | AAGTAAAAGA | TGCTGAAGAT | CAGTTGGGTG | 1980
| CACGAGTGGG | TTACATCGAA | CTGGATCTCA | ACAGCGGTAA | GATCCTTGAG | AGTTTTCGCC | 2040
| CCGAAGAACG | TTTTCCAATG | ATGAGCACTT | TTAAAGTTCT | GCTATGTGGC | GCGGTATTAT | 2100
| CCCGTATTGA | CGCCGGGCAA | GAGCAACTCG | GTCGCCGCAT | ACACTATTCT | CAGAATGACT | 2160
| TGGTTGAGTA | CTCACCAGTC | ACAGAAAAGC | ATCTTACGGA | TGGCATGACA | GTAAGAGAAT | 2220
| TATGCAGTGC | TGCCATAACC | ATGAGTGATA | ACACTGCGGC | CAACTTACTT | CTGACAACGA | 2280
| TCGGAGGACC | GAAGGAGCTA | ACCGCTTTTT | TGCACAACAT | GGGGGATCAT | GTAACTCGCC | 2340
| TTGATCGTTG | GGAACCGGAG | CTGAATGAAG | CCATACCAAA | CGACGAGCGT | GACACCACGA | 2400
| TGCCTGTAGC | AATGGCAACA | ACGTTGCGCA | AACTATTAAC | TGGCGAACTA | CTTACTCTAG | 2460
| CTTCCCGGCA | ACAATTAATA | GACTGGATGG | AGGCGGATAA | AGTTGCAGGA | CCACTTCTGC | 2520
| GCTCGGCCCT | TCCGGCTGGC | TGGTTTATTG | CTGATAAATC | TGGAGCCGGT | GAGCGTGGGT | 2580
| CTCGCGGTAT | CATTGCAGCA | CTGGGGCCAG | ATGGTAAGCC | CTCCCGTATC | GTAGTTATCT | 2640
| ACACGACGGG | GAGTCAGGCA | ACTATGGATG | AACGAAATAG | ACAGATCGCT | GAGATAGGTG | 2700
| CCTCACTGAT | TAAGCATTGG | TAACTGTCAG | ACCAAGTTTA | CTCATATATA | CTTTAGATTG | 2760
| ATTTAAAACT | TCATTTTTAA | TTTAAAAGGA | TCTAGGTGAA | GATCCTTTTT | GATAATCTCA | 2820
| TGACCAAAAT | CCCTTAACGT | GAGTTTTCGT | TCCACTGAGC | GTCAGACCCC | GTAGAAAAGA | 2880
| TCAAAGGATC | TTCTTGAGAT | CCTTTTTTTC | TGCGCGTAAT | CTGCTGCTTG | CAAACAAAAA | 2940
| AACCACCGCT | ACCAGCGGTG | GTTTGTTTGC | CGGATCAAGA | GCTACCAACT | CTTTTTCCGA | 3000
| AGGTAACTGG | CTTCAGCAGA | GCGCAGATAC | CAAATACTGT | CCTTCTAGTG | TAGCCGTAGT | 3060
| TAGGCCACCA | CTTCAAGAAC | TCTGTAGCAC | CGCCTACATA | CCTCGCTCTG | CTAATCCTGT | 3120
| TACCAGTGGC | TGCTGCCAGT | GGCGATAAGT | CGTGTCTTAC | CGGGTTGGAC | TCAAGACGAT | 3180
| AGTTACCGGA | TAAGGCGCAG | CGGTCGGGCT | GAACGGGGGG | TTCGTGCACA | CAGCCCAGCT | 3240
| TGGAGCGAAC | GACCTACACC | GAACTGAGAT | ACCTACAGCG | TGAGCTATGA | GAAAGCGCCA | 3300
| CGCTTCCCGA | AGGGAGAAAG | GCGGACAGGT | ATCCGGTAAG | CGGCAGGGTC | GGAACAGGAG | 3360
| AGCGCACGAG | GGAGCTTCCA | GGGGGAAACG | CCTGGTATCT | TTATAGTCCT | GTCGGGTTTC | 3420
| GCCACCTCTG | ACTTGAGCGT | CGATTTTTGT | GATGCTCGTC | AGGGGGGCGG | AGCCTATGGA | 3480
| AAAACGCCAG | CAACGCGGCC | TTTTTACGGT | TCCTGGCCTT | TTGCTGGCCT | TTTGCTCACA | 3540
| TGTTCTTTCC | TGCGTTATCC | CCTGATTCTG | TGGATAACCG | TATTACCGCC | TTTGAGTGAG | 3600
| CTGATACCGC | TCGCCGCAGC | CGAACGACCG | AGCGCAGCGA | GTCAGTGAGC | GAGGAAGCGG | 3660
| AAGA | | | | | | 3664

( 2 ) INFORMATION FOR SEQ ID NO: 2:

( i ) SEQUENCE CHARACTERISTICS:
        ( A ) LENGTH: 3832 bases
        ( B ) TYPE: nucleic acid
        ( C ) STRANDEDNESS: single
        ( D ) TOPOLOGY: linear ( x i ) SEQUENCE DESCRIPTION: SEQ ID NO: 2:

| | | | | | |
|---|---|---|---|---|---|
| ACCCGACACC | ATCGAATGGC | GCAAAACCTT | TCGCGGTATG | GCATGATAGC | GCCCGGAAGA | 60
| GAGTCAATTC | AGGGTGGTGA | ATGTGAAACC | AGTAACGTTA | TACGATGTCG | CAGAGTATGC | 120
| CGGTGTCTCT | TATCAGACCG | TTTCCCGCGT | GGTGAACCAG | GCCAGCCACG | TTTCTGCGAA | 180
| AACGCGGGAA | AAAGTGGAAG | CGGCGATGGC | GGAGCTGAAT | TACATTCCCA | ACCGCGTGGC | 240

| | | | | | |
|---|---|---|---|---|---|
| ACAACAACTG | GCGGGCAAAC | AGTCGTTGCT | GATTGGCGTT | GCCACCTCCA | GTCTGGCCCT | 300 |
| GCACGCGCCG | TCGCAAATTG | TCGCGGCGAT | TAAATCTCGC | GCCGATCAAC | TGGGTGCCAG | 360 |
| CGTGGTGGTG | TCGATGGTAG | AACGAAGCGG | CGTCGAAGCC | TGTAAAGCGG | CGGTGCACAA | 420 |
| TCTTCTCGCG | CAACGCGTCA | GTGGGCTGAT | CATTAACTAT | CCGCTGGATG | ACCAGGATGC | 480 |
| CATTGCTGTG | GAAGCTGCCT | GCACTAATGT | TCCGGCGTTA | TTTCTTGATG | TCTCTGACCA | 540 |
| GACACCCATC | AACAGTATTA | TTTTCTCCCA | TGAAGACGGT | ACGCGACTGG | GCGTGGAGCA | 600 |
| TCTGGTCGCA | TTGGGTCATC | AGCAAATCGC | GCTGTTAGCG | GCCCATTAA | GTTCTGTCTC | 660 |
| GGCGCGTCTG | CGTCTGGCTG | GCTGGCATAA | ATATCTCACT | CGCAATCAAA | TTCAGCCGAT | 720 |
| AGCGGAACGG | GAAGGCGACT | GGAGTGCCAT | GTCCGGTTTT | CAACAAACCA | TGCAAATGCT | 780 |
| GAATGAGGGC | ATCGTTCCCA | CTGCGATGCT | GGTTGCCAAC | GATCAGATGG | CGCTGGGCGC | 840 |
| AATGCGCGCC | ATTACCGAGT | CCGGGCTGCG | CGTTGGTGCG | GATATCTCGG | TAGTGGGATA | 900 |
| CGACGATACC | GAAGACAGCT | CATGTTATAT | CCCGCCGTTA | ACCACCATCA | AACAGGATTT | 960 |
| TCGCCTGCTG | GGGCAAACCA | GCGTGGACCG | CTTGCTGCAA | CTCTCTCAGG | GCCAGGCGGT | 1020 |
| GAAGGGCAAT | CAGCTGTTGC | CCGTCTCACT | GGTGAAAAGA | AAACCACCC | TGGCGCCCAA | 1080 |
| TACGCAAACC | GCCTCTCCCC | GCGCGTTGGC | CGATTCATTA | ATGCAGCTGG | CACGACAGGT | 1140 |
| TTCCGACTG | GAAAGCGGGC | AGTGAGCGCA | ACGCAATTAA | TGTGAGTTAG | CTCACTCATT | 1200 |
| AGGCACCCCA | GGCTTTACAC | TTTATGCTTC | CGGCTCGTAT | GTTGTGTGGA | ATTGTGAGCG | 1260 |
| GATAACAATT | TCACACAGGA | AACAGCTATG | ACCATGATTA | CGAATTTCTA | GATAACGAGG | 1320 |
| GCAAAAAATG | AAAAAGACAG | CTATCGCGAT | TGCAGTGGCA | CTGGCTGGTT | TCGCTACCGT | 1380 |
| AGCGCAGGCC | TGAGACCAGA | ATTCGAGCTC | GGTACCCGGG | GATCCCTCGA | GGTCGACCTG | 1440 |
| CAGGCAGCGC | TTGGCGTCAC | CCGCAGTTCG | GTGGTTAATA | AGCTTGACCT | GTGAAGTGAA | 1500 |
| AAATGGCGCA | CATTGTGCGA | CATTTTTTT | GTCTGCCGTT | TACCGCTACT | GCGTCACGGA | 1560 |
| TCTCCACGCG | CCCTGTAGCG | GCGCATTAAG | CGCGGCGGGT | GTGGTGGTTA | CGCGCAGCGT | 1620 |
| GACCGCTACA | CTTGCCAGCG | CCCTAGCGCC | CGCTCCTTTC | GCTTTCTTCC | CTTCCTTTCT | 1680 |
| CGCCACGTTC | GCCGGCTTTC | CCCGTCAAGC | TCTAAATCGG | GGGCTCCCTT | TAGGGTTCCG | 1740 |
| ATTTAGTGCT | TTACGGCACC | TCGACCCCAA | AAAACTTGAT | TAGGGTGATG | GTTCACGTAG | 1800 |
| TGGGCCATCG | CCCTGATAGA | CGGTTTTTCG | CCCTTTGACG | TTGGAGTCCA | CGTTCTTTAA | 1860 |
| TAGTGGACTC | TTGTTCCAAA | CTGGAACAAC | ACTCAACCCT | ATCTCGGTCT | ATTCTTTTGA | 1920 |
| TTTATAAGGG | ATTTTGCCGA | TTTCGGCCTA | TTGGTTAAAA | AATGAGCTGA | TTTAACAAA | 1980 |
| ATTTAACGCG | AATTTTAACA | AAATATTAAC | GTTACAATT | TCAGGTGGCA | CTTTTCGGGG | 2040 |
| AAATGTGCGC | GGAACCCCTA | TTTGTTTATT | TTTCTAAATA | CATTCAAATA | TGTATCCGCT | 2100 |
| CATGAGACAA | TAACCCTGAT | AAATGCTTCA | ATAATATTGA | AAAAGGAAGA | GTATGAGTAT | 2160 |
| TCAACATTTC | CGTGTCGCCC | TTATTCCCTT | TTTTGCGGCA | TTTTGCCTTC | CTGTTTTTGC | 2220 |
| TCACCCAGAA | ACGCTGGTGA | AAGTAAAAGA | TGCTGAAGAT | CAGTTGGGTG | CACGAGTGGG | 2280 |
| TTACATCGAA | CTGGATCTCA | ACAGCGGTAA | GATCCTTGAG | AGTTTTCGCC | CCGAAGAACG | 2340 |
| TTTTCCAATG | ATGAGCACTT | TTAAAGTTCT | GCTATGTGGC | GCGGTATTAT | CCCGTATTGA | 2400 |
| CGCCGGGCAA | GAGCAACTCG | GTCGCCGCAT | ACACTATTCT | CAGAATGACT | TGGTTGAGTA | 2460 |
| CTCACCAGTC | ACAGAAAAGC | ATCTTACGGA | TGGCATGACA | GTAAGAGAAT | TATGCAGTGC | 2520 |
| TGCCATAACC | ATGAGTGATA | ACACTGCGGC | CAACTTACTT | CTGACAACGA | TCGGAGGACC | 2580 |
| GAAGGAGCTA | ACCGCTTTTT | TGCACAACAT | GGGGGATCAT | GTAACTCGCC | TTGATCGTTG | 2640 |

-continued

| | | | | | | |
|---|---|---|---|---|---|---|
| GGAACCGGAG | CTGAATGAAG | CCATACCAAA | CGACGAGCGT | GACACCACGA | TGCCTGTAGC | 2700 |
| AATGGCAACA | ACGTTGCGCA | AACTATTAAC | TGGCGAACTA | CTTACTCTAG | CTTCCCGGCA | 2760 |
| ACAATTAATA | GACTGGATGG | AGGCGGATAA | AGTTGCAGGA | CCACTTCTGC | GCTCGGCCCT | 2820 |
| TCCGGCTGGC | TGGTTTATTG | CTGATAAATC | TGGAGCCGGT | GAGCGTGGCT | CTCGCGGTAT | 2880 |
| CATTGCAGCA | CTGGGGCCAG | ATGGTAAGCC | CTCCCGTATC | GTAGTTATCT | ACACGACGGG | 2940 |
| GAGTCAGGCA | ACTATGGATG | AACGAAATAG | ACAGATCGCT | GAGATAGGTG | CCTCACTGAT | 3000 |
| TAAGCATTGG | TAACTGTCAG | ACCAAGTTTA | CTCATATATA | CTTTAGATTG | ATTTAAAACT | 3060 |
| TCATTTTTAA | TTTAAAAGGA | TCTAGGTGAA | GATCCTTTTT | GATAATCTCA | TGACCAAAAT | 3120 |
| CCCTTAACGT | GAGTTTTCGT | TCCACTGAGC | GTCAGACCCC | GTAGAAAAGA | TCAAAGGATC | 3180 |
| TTCTTGAGAT | CCTTTTTTTC | TGCGCGTAAT | CTGCTGCTTG | CAAACAAAAA | AACCACCGCT | 3240 |
| ACCAGCGGTG | GTTTGTTTGC | CGGATCAAGA | GCTACCAACT | CTTTTTCCGA | AGGTAACTGG | 3300 |
| CTTCAGCAGA | GCGCAGATAC | CAAATACTGT | CCTTCTAGTG | TAGCCGTAGT | TAGGCCACCA | 3360 |
| CTTCAAGAAC | TCTGTAGCAC | CGCCTACATA | CCTCGCTCTG | CTAATCCTGT | TACCAGTGGC | 3420 |
| TGCTGCCAGT | GGCGATAAGT | CGTGTCTTAC | CGGGTTGGAC | TCAAGACGAT | AGTTACCGGA | 3480 |
| TAAGGCGCAG | CGGTCGGGCT | GAACGGGGGG | TTCGTGCACA | CAGCCCAGCT | TGGAGCGAAC | 3540 |
| GACCTACACC | GAACTGAGAT | ACCTACAGCG | TGAGCTATGA | GAAAGCGCCA | CGCTTCCCGA | 3600 |
| AGGGAGAAAG | GCGGACAGGT | ATCCGGTAAG | CGGCAGGGTC | GGAACAGGAG | AGCGCACGAG | 3660 |
| GGAGCTTCCA | GGGGGAAACG | CCTGGTATCT | TTATAGTCCT | GTCGGGTTTC | GCCACCTCTG | 3720 |
| ACTTGAGCGT | CGATTTTTGT | GATGCTCGTC | AGGGGGGCGG | AGCCTATGGA | AAAACGCCAG | 3780 |
| CAACGCGGCC | TTTTTACGGT | TCCTGGCCTT | TTGCTGGCCT | TTTGCTCACA | TG | 3832 |